United States Patent
Constantz et al.

[11] Patent Number: 6,083,229
[45] Date of Patent: Jul. 4, 2000

[54] METHODS AND DEVICES FOR THE PREPARATION, STORAGE AND ADMINISTRATION OF CALCIUM PHOSPHATE CEMENTS

[75] Inventors: Brent R. Constantz, Portola Valley; Ben Clawson, Soquel, both of Calif.

[73] Assignee: Norian Corporation, Cupertino, Calif.

[21] Appl. No.: 09/183,920

[22] Filed: Oct. 30, 1998

Related U.S. Application Data

[63] Continuation of application No. 08/989,845, Dec. 12, 1997
[60] Provisional application No. 60/032,726, Dec. 13, 1996, provisional application No. 60/046,684, May 16, 1997, provisional application No. 60/055,162, Aug. 11, 1997, provisional application No. 60/055,163, Aug. 11, 1997, provisional application No. 60/064,612, Nov. 7, 1997, provisional application No. 60/065,345, Nov. 12, 1997, and provisional application No. 60/065,342, Nov. 12, 1997.

[51] Int. Cl.⁷ .................................................. A61B 17/58
[52] U.S. Cl. .............................. 606/92; 604/87; 206/219
[58] Field of Search ................................. 606/92, 93, 94; 604/87, 89, 416, 410; 206/219

[56] References Cited

U.S. PATENT DOCUMENTS

| | | | |
|---|---|---|---|
| 3,610,586 | 10/1971 | Price | 206/219 |
| 3,983,994 | 10/1976 | Wyslotsky | 206/219 |
| 4,149,633 | 4/1979 | Nilson | 206/219 |
| 4,185,072 | 1/1980 | Puderbaugh et al. | 422/99 |
| 4,338,925 | 7/1982 | Miller | 128/92 |
| 4,458,811 | 7/1984 | Wilkinson | 206/219 |
| 4,463,875 | 8/1984 | Tepic | 222/82 |
| 4,465,478 | 8/1984 | Sabelman et al. | 604/224 |
| 4,467,588 | 8/1984 | Carveth | 53/425 |
| 4,537,308 | 8/1985 | Hollander, Jr. | 206/484 |
| 4,540,089 | 9/1985 | Maloney | 206/219 |
| 4,576,152 | 3/1986 | Muller et al. | 128/92 R |
| 4,591,357 | 5/1986 | Sneider | 604/416 |
| 4,602,910 | 7/1986 | Larkin | 604/87 |
| 4,608,043 | 8/1986 | Larkin | 604/87 |
| 4,671,263 | 6/1987 | Draenert | 128/92 VO |
| 4,787,511 | 11/1988 | McIver | 206/219 |
| 4,795,265 | 1/1989 | Dahlberg et al. | 366/69 |
| 4,798,288 | 1/1989 | Holzner | 206/222 |
| 4,815,454 | 3/1989 | Dozier, Jr. | 128/92 VO |
| 4,927,012 | 5/1990 | Rowe | 206/219 |
| 4,952,068 | 8/1990 | Flint | 366/337 |
| 4,973,168 | 11/1990 | Chan | 206/219 |
| 4,994,065 | 2/1991 | Gibbs et al. | 606/92 |
| 4,997,083 | 3/1991 | Loretti et al. | 206/219 |
| 5,058,770 | 10/1991 | Herold et al. | 222/80 |
| 5,069,773 | 12/1991 | Frangioni | 204/299 R |
| 5,176,634 | 1/1993 | Smith et al. | 604/87 |
| 5,287,961 | 2/1994 | Herran | 206/219 |
| 5,304,147 | 4/1994 | Johnson et al. | 604/183 |
| 5,370,221 | 12/1994 | Magnusson et al. | 206/221 |
| 5,398,483 | 3/1995 | Smith et al. | 53/474 |
| 5,423,421 | 6/1995 | Inoue et al. | 206/219 |
| 5,431,496 | 7/1995 | Balteau et al. | 383/38 |
| 5,431,654 | 7/1995 | Nic | 606/92 |
| 5,462,526 | 10/1995 | Barney et al. | 604/85 |
| 5,549,380 | 8/1996 | Lidgren et al. | 366/139 |
| 5,551,778 | 9/1996 | Hauke et al. | 366/139 |

Primary Examiner—Michael Buiz
Assistant Examiner—Julian W. Woo
Attorney, Agent, or Firm—Bozicevic, Field & Francis; Bret Field

[57] ABSTRACT

A system is provided for the storage, preparation and administration of calcium phosphate cements. The subject invention provides a storage means for storing a two component calcium phosphate cement having a liquid component and a dry component. Also provided is a preparation means for combining the two components of the cement while present in the storage means. The subject invention further provides a means for administering the prepared cement to a physiological site. The subject devices and methods find use in a variety of applications where the introduction of a flowable material capable of setting to a solid calcium phosphate mineral to a physiological site is desired, including dental and orthopedic applications.

19 Claims, 18 Drawing Sheets

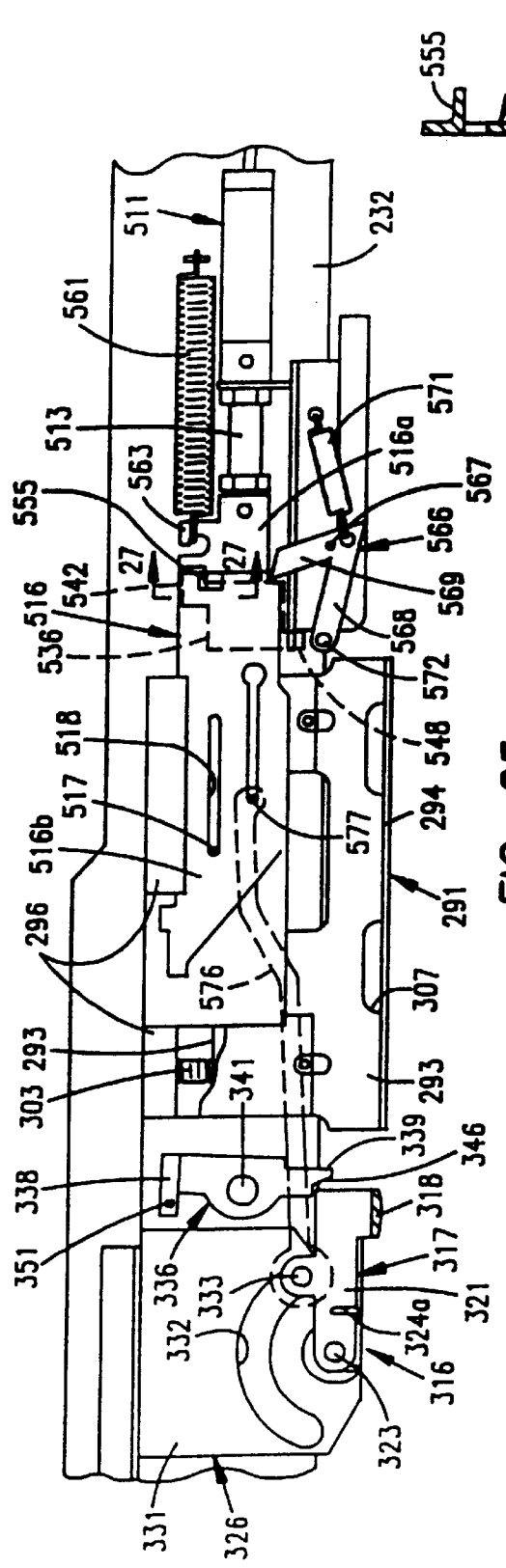
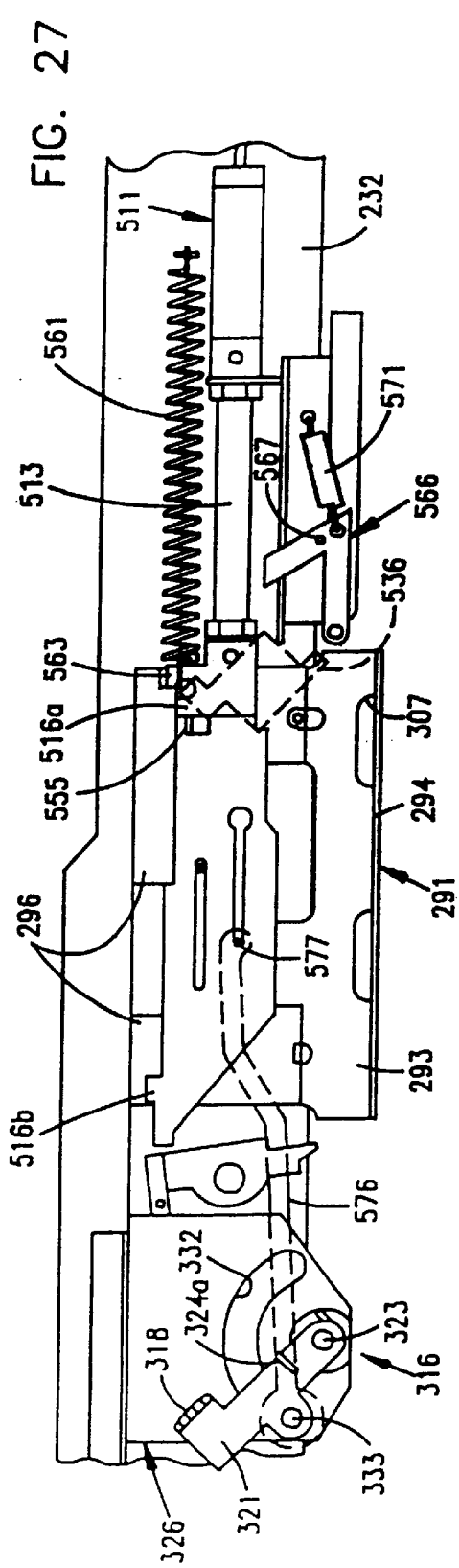

METHODS AND DEVICES FOR THE PREPARATION, STORAGE AND ADMINISTRATION OF CALCIUM PHOSPHATE CEMENTS

CROSS-REFERENCE TO RELATED APPLICATIONS

This application is: a continuation in part of application Ser. No. 60/032,726, filed Dec. 13, 1996; and a continuation in part of application Ser. No. 60/046,684, filed May 16, 1997; and a continuation in part of application Ser. No. 60/055,162, filed Aug. 11, 1997; and a continuation in part of application Ser. No. 60/055,163, filed Aug. 11, 1997; and a continuation in part of application Ser. No. 60/064,612, filed Nov. 7, 1997; and a continuation in part of application Ser. No. 60/065,345 (Att'y docket no. NOR-14PRV8) filed Nov. 12, 1997; and a continuation in part of application Ser. No. 60/065,342 (Att'y docket no. NOR-14PRV9) filed Nov. 12, 1997; the disclosures of which applications are herein incorporated by reference.

INTRODUCTION

TECHNICAL FIELD

This technical field of this invention is calcium phosphate cements.

BACKGROUND OF THE INVENTION

Calcium phosphate cements which are prepared by combining a dry component(s) and a liquid to form a flowable paste like material that is subsequently capable of setting into a solid calcium phosphate product hold great promise for use as structural materials in the orthopedic and dental fields. For example, it is desirable to be able to inject a flowable material into a cancellous bone void and have the material set into a solid calcium phosphate mineral product that is capable of withstanding physiological loads. Materials that set into solid calcium phosphate mineral products are of particular interest as such products can closely resemble the mineral phase of natural bone and are susceptible to remodeling, making such products extremely attractive for use in orthopedics and related fields.

Calcium phosphate cements that have been developed to date, while capable of setting in vivo into a product that resembles the mineral phase of natural bone and providing the benefits described above, have been less than ideal in terms of their preparation and methods of use. Specifically, cements that have been developed and marketed to date have required the user, such as the doctor, nurse or other health care practitioner, to manually combine the various components of the cement in a sterile field, load the resultant paste into a suitable delivery device such as a syringe, and then introduce the paste to a physiological site of interest.

Disadvantages associated with these present methods of preparing and using calcium phosphate cements include the requirement that the entire preparation process be carried out in a sterile field, the potential for inadequate or suboptimum mixing of the various components, and the overall number of different steps required and the concomitant time requirements placed on the health care practitioners.

Accordingly, there is great interest in the development of improved systems for the storage, preparation and delivery of a calcium phosphate cement to a physiological site of interest. Ideally such a system should provide for long term storage of the components in a convenient and easy to use format. Such a system should also provide for automatic and complete combination of the various cement components, preferably in a non-sterile field while maintaining the sterility of the cement being prepared. Finally, such a system should provide for easy and controllable delivery of the components to a site of interest without having to substantially expose the cement to the environment and/or manually pack the cement into the delivery means.

Relevant Literature

U.S. Pat. Nos. 4,795,265; 5,370,221 and 5,423,421 disclose two component storage and/or preparation means.

SUMMARY OF THE INVENTION

A system is provided for the storage, preparation and administration of calcium phosphate cements. The subject invention provides a storage means for two component calcium phosphate cements. Also provided is a preparation means for combining the two components of the cement while present in the storage means. The subject invention further provides a means for administering the prepared cement to a bone repair site. The subject devices and methods find use in a variety of applications in which it is desired to introduce a flowable material capable of setting into a calcium phosphate mineral to a physiological site, including dental and orthopedic applications.

BRIEF DESCRIPTION OF THE FIGURES

FIG. 25 is a fragmentary elevational view, partially cut away and rotated 180°, of the mixing apparatus of FIG. 7 taken along the line 25—25 of FIG. 13.

FIG. 26 is a fragmentary elevational view, similar to FIG. 25, of the mixing apparatus of FIG. 7 in another position.

FIG. 27 is a fragmentary cross-sectional view of the mixing apparatus of FIG. 7 taken along the line 27—27 of FIG. 25.

DESCRIPTION OF THE SPECIFIC EMBODIMENTS

Figure 1:
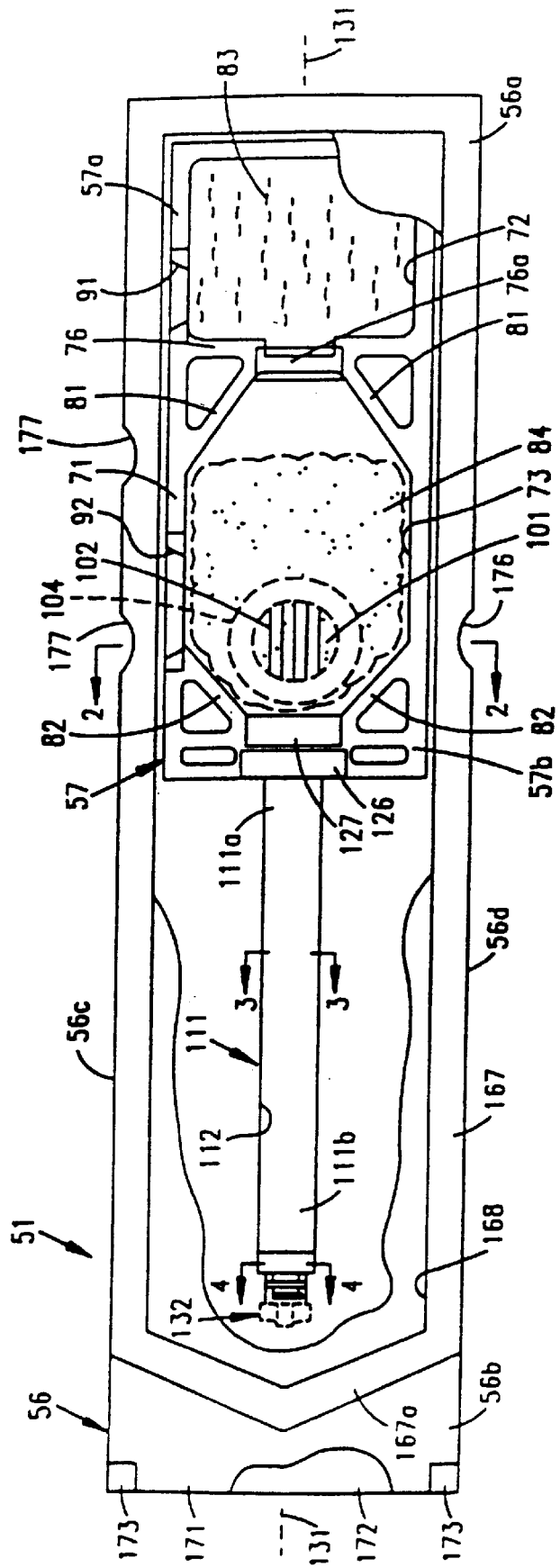
FIG. 1 is a top plan view, partially cut away, of the storage means of the present invention.

Systems are provided for the storage, preparation and administration of calcium phosphate cements to a bone repair site. The subject invention provides a storage means for storing a two component calcium phosphate cement having a liquid component and a dry component. Also provided is a preparation means for combining the two components of the cement while present in the storage means, where the device comprises a means. The subject invention further provides a means for administering the prepared cement to a physiological site. The subject devices and methods find use in a variety of applications where the introduction of a flowable material capable of setting to a solid calcium phosphate mineral to a physiological site is desired, including dental and orthopedic applications. In further describing the subject invention, the various components of the invention will first be discussed in general terms followed by a more detailed description of a preferred embodiment of the invention in terms of the figures. These discussions will then be followed by a description of the various applications in which the subject invention finds use.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

The subject invention provides a system for the storage, preparation and administration of a calcium phosphate cement to a physiological site. By the term "system" is meant the working combination of the enumerated components thereof, which components include the storage means, the mixing device and the delivery device.

The storage means of the subject invention is capable of at least: (a) storing a two component cement having a liquid component and dry component in a sterile environment; and (b) serving as a sterile environment for the combination of the two components.

Two component cements capable of being stored in the subject storage means comprise a dry component and a liquid component that are capable of being combined into a flowable paste material that is capable of setting in vivo into a solid product. The flowable, paste-like material is capable of setting up into a solid structural material in a physiological environment such as that found in the cancellous bone region of mammalian bones, particularly human bones. Of interest are materials that are capable of isothermic setting, are biocompatible, bioresorbable and, more particularly remodelable and capable of achieving a compressive strength sufficient to counter physiological loads within 12 to 24 hours of implantation, where sufficient compressive strength will be at least about 30, and more usually at least about 40 mPa, and in many embodiments will be at least about 50 mPa. Preferred structural materials are calcium phosphate cements.

Calcium phosphate cements suitable for use in the subject methods will be flowable for an initial period of time following preparation and be capable of setting in an in vivo fluid environment into a solid apatitic product. The subject cements will comprise dry components and a liquid component which, upon combination, form a paste-like flowable composition capable of setting into a calcium phosphate apatitic material, preferably hydroxyapatite, and more preferably a carbonated apatite, i.e. dahlite, having a carbonate substitution of from 2 to 10%, usually 2 to 8% by weight of the final product. Calcium phosphate cements which are suitable for use in the subject methods include those cements described in U.S. Pat. Nos. 4,880,610; 5,047,031; 5,129,905; 5,336,264; 5,053,212; 5,178,845; 5,580,623; 5,569,442; 5,571,493 and 5,496,399, the disclosures of which are herein incorporated by reference.

The dry components of the cements suitable for use in the subject methods will comprise at least a calcium source and a phosphate source. The phosphate source will generally be a partially neutralized phosphoric acid source free of uncombined water, where such sources include monocalcium phosphate anhydrous, monocalcium phosphate monohydrate, dicalcium phosphate, dicalcium phosphate dihydrate and the like, where in some embodiments partially neutralized phosphoric acid sources which are neutralized up to and including the first proton are preferred, such as monocalcium phosphate and its monohydrate (i.e. MCP and MCPM). A variety of calcium sources may be employed, where the calcium sources may or may not include a source of carbonate. Suitable calcium sources include tetracalcium phosphate, tricalcium phosphates, amorphous calcium phosphates and the like. Preferably, the dry components will further comprise a source of carbonate ion, where the source may be combined with a calcium source, e.g. $CaCO_3$ or carbonated amorphous calcium phosphate.

In many preferred embodiments, the dry components of the cements employed in the subject methods preferably comprise a homogeneous storage stable mixture of calcium carbonate, tricalcium phosphate, preferably α-tricalcium phosphate, more preferably reactive α-tricalcium phosphate, as described in U.S. Pat. No. 5,569,442 the disclosure of which is herein incorporated by reference, and monocalcium phosphate monohydrate. Generally, calcium carbonate will be present in the cement in an amount ranging from about 5 to 25 wt. %, usually from about 5 to 20 wt. %, and more usually 10 to 20 wt. % of the entire weight of the dry components. The α-tricalcium phosphate component will be present in an amount ranging from about 60 to 95 wt. %, usually from about 65 to 90 wt. % and more usually from about 70 to 90 wt. % of the entire weight of the dry components. Of particular interest for the α-tricalcium phosphate is the reactive α-tricalcium phosphate described in U.S. Pat. No. 5,569,442, the disclosure of which is herein incorporated by reference. The monocalcium phosphate monohydrate component will be present in an amount ranging from about 1 to 20 wt. %, usually from about 1 to 15 wt. % and more usually from about 2 to 15 wt. % of the entire weight of the dry components.

As described above, the cement will comprise a liquid component, e.g. setting solution or lubricant, in addition to the dry components described above where the lubricant may be pure water or be an aqueous solution comprising one or more ions. Preferably the setting solution will be a carbonate or phosphate containing solution at a pH in the range of 6 to 11, preferably 7 to 9, wherein the concentration of carbonate or phosphate in the solution will preferably range from 0.05 to 0.5 molal (m), with a 0.05 to 0.1 molal (m) sodium phosphate solution being particularly preferred. The setting solution or lubricant may further comprise one or more modification agents which modulate the properties of the cement, such as polymeric agents, e.g. proteinaceous agents, and the like.

The storage means comprises: (a) a first compartment capable of storing a liquid, e.g. the liquid component of a two component cement; (b) a second storage compartment capable of storing a dry powder, e.g. the dry component of a two component cement; and (c) a third elongate compartment that is capable of receiving a flowable paste like material which is produced upon combination of the liquid and dry component. The first, second and third compartments are separated from each other by frangible barriers, such that the contents of one compartment can be moved to another compartment upon application of a force of sufficient magnitude to burst the frangible barrier. Importantly, the device is capable of maintaining all of the compartments and the contents thereof in a sterile environment.

The first compartment has a volume sufficient to contain the liquid component of the two components cement, where the volume is sufficient to hold from about 5 to 25, usually from about 5 to 20 grams. The container has a shape which promotes the movement of substantially all of the liquid into the second container. Suitable shapes include square, rectangular, curved, triangular, irregular and the like, where the container will typically have rectangular or square shape with rounded or smoothed corners.

The second compartment has a volume sufficient to at least house the dry component and the liquid component and provide sufficient space for the combination of the two components, where the volume will typically be sufficient to house from about 5 to 100, usually from about 5 to 50 grams of material. As with the first container, the second container has a shape which promotes the movement of substantially all of the combined material into the third compartment, and is generally square, rectangular or octagonal with a rounded or smoothed corners. In addition, the second compartment has a shape that promotes thorough mixing of the dry and liquid components, e.g. which prevents incomplete mixing, i.e. such that no dry powder remains following combination of the liquid and dry components. Preferably, the second compartment comprises a means for selectively releasing gas from the interior of the compartment while retaining the other contents in the container, where such means may be a vent or other suitable means.

The third compartment of the storage or packaging means is an elongate compartment, usually a tubular or cylindrical container, which is capable of receiving the flowable product produced upon combination of the liquid and dry components in the second compartment of the storage means. As such, the third elongate compartment has a volume which is typically commensurate with the volume of the second compartment, not varying by more than about 50%, usually not varying by more than about 30%. The third compartment preferably comprises a fitment means at its distal end for attaching a needle or analogous delivery device and providing for flow of the material from the compartment to the delivery means. The fitment means will preferably be capable of providing for locking engagement of the needle with the third compartment such that it is movable between a locked and unlocked position, e.g. by a quarter turn.

Separating the first and second compartments is a first frangible or burstable barrier through which the liquid component present in the first container can be selectively moved into the second container upon application of an appropriate amount of force or other movement means to the liquid contents of the first container. An analogous frangible barrier separates the second and third compartments and provides for retention of the contents of the second compartment during combination of the first and second components of the cement but allow for passage of the combined flowable product into the third compartment upon application of the appropriate movement force to the contents of the second compartment. The frangible barriers or seats are fabricated from any suitable material, where suitable materials include heat pressure activated adhesives and plastics, e.g. polyethylenes, gel lacquers, DE/DVA alloys, and the like.

The various components of the storage means described above are preferably contained in a containment means which ensures the sterility of the contents of the storage means and is at least partially removable in a manner sufficient to expose substantially all of the third elongate container, where by at least partially removable is meant that the containment means may be pealed back to expose the third elongate member.

The various elements of the storage device will generally be fabricated, at least partially, from an inert polymeric material, as described in greater detail below in terms of the figures, where suitable polymeric materials include poly (ethylene) and blends thereof, polyesters, nylon, EVA and the like. Incorporated into the packaging means may be various non-polymeric materials which serve to protect the contents of the various containers, where such non-polymeric materials include foils, Si—O, and the like. Also present in the storage means may be various adhesives, where suitable adhesives include acrylic and gel lacquers, and the like.

The storage means may be prepared using any convenient methodology. One methodology of interest is to use two initial polymeric sheets and heat seal them together in a fashion which results in the production of the various compartments and other elements of the storage means, as described in greater detail below. During fabrication, sealable entry ports will be provided for introducing the liquid and dry components into the first and second compartments respectively, where these components may be introduced manually or using an automatic packaging device, such as described in greater detail below.

Also provided by the subject invention is a mixing device for combining the two components of the cement into a flowable product in the storage means or package, specifically in the second compartment of the package, under sterile conditions. Critical elements of the mixing device are: (a) a means for moving the liquid component from the first to the second compartment; (b) a means for thoroughly mixing the dry and liquid components in the second compartment; and (c) a means for moving the flowable product produced by combination of the liquid and dry components from the second compartment to the third elongate compartment of the storage means. Preferably, the mixing device will further comprise a means for positioning the storage means in the device such that it is in a stable, i.e. non movable, position during mixing of the contents of the storage means.

The means for moving the liquid component from the first compartment may be any means capable of applying sufficient force to the liquid component such that it bursts through the frangible barrier into the second compartment comprising the dry component of the two component cement. The means will also prevent backflow of the liquid from the second compartment into the first compartment. Suitable means include a squeegee or roller that moves the liquid from the first compartment into the second compartment coupled with a clamp or similar device which prevents backflow of liquid into the first compartment. One preferred means comprises a substantially planar element, such as a plate having a substantially planar surface, which is compressed onto the first compartment and maintained in the compressed positioned such that the liquid or fluid component is forced out of the first compartment and into the second compartment through the frangible seal, where backflow of the liquid into the first compartment is prevented through compression of the second compartment by the plate.

The second critical element of the mixing device is the means for thoroughly mixing the dry and liquid components in the second compartment. This mixing means is capable of introducing sufficient shear force to the contents of the second compartment such that the liquid and powder components are substantially completely combined to produce the flowable product capable of setting into a solid calcium phosphate mineral in vivo, where the mixing means is such that substantially no uncombined reactants, such as uncombined powder, remains following combination of the solid and liquid components. In a preferred embodiment, the mixing means comprises at least two grooved rollers which are movable across the second compartment in a manner which provides for the requisite substantially thorough combination of the dry and liquid components. In this embodiment, the device will randomize the movement of the grooved rollers across the contents of the second compartment, where by randomize is meant that the grooved rollers traverse a different path with respect to the second container each time they pass over it. The device may comprise a means for providing this randomized movement of the grooved rollers, which such means may be an indexing means which alters the initial position of the rollers prior to each pass over the compartment.

The third component of the subject mixing device is a means for moving the flowable product from the second compartment to the third elongated compartment. As with the first movement means described above, this second movement means is capable of applying a sufficient movement force to the flowable product to move substantially all of the contents of the second container through the frangible barrier into the third elongate compartment. In a preferred embodiment, this second movement means is typically a roller or squeegee that moves the flowable product from the second container into the third container. Preferably, the second movements means also at least inhibits, if not prevents, backflow of the flowable product from the third to the second container.

Generally, the mixing device further comprises a positioning means that serves to maintain the storage means comprising the two component cement in a static position within the device during mixing. The positioning means usually comprises a planar surface on which the storage means is placed during mixing, where the planar surface will usually comprise a depressed or grooved region. Other positioning means may also be present, such as ridges, pegs, flaps or other holding elements, as may be convenient and desired.

The mixer device also usually comprises an actuation means for moving the various elements of the device during mixing. Any convenient actuation means may be employed, where two such actuation means include electronic actuation means and a pneumatic actuation means, such as a pneumatic air system, where such actuation means can be configured in any suitable fashion according to the knowledge of those of skill in the art.

Other elements that may be present in the device include a means for displaying the various mixing stages to the user, e.g. a display for alerting the user as to when mixing is completed, such as a digital display, readout, series of diodes, where the choice of display will be a matter of convenience and is not critical to the invention. The device may further comprise a power source, such as a battery.

The various elements of the mixing device are conveniently housed in an openable housing configuration having a lid and base plate in releasable relationship to each other and joined by a hinge, where the baseplate serves as a support for the storage means or package during mixing and the lid or cover comprises the mixing and movement elements, as described above, in a manner such that upon closure of the lid onto the base plate these elements can be moved into contact with the storage means as required during preparation of the two component cement.

In using the mixing device to prepare the two component cement while present in the storage means, the storage means is placed onto the positioning means of the device, e.g. the bottom or base plate. Where the mixing and/or movement means are present on a closeable lid, as described above, the next step is closure of the lid of the device. The first movement means is then actuated in a manner sufficient to force substantially all of the liquid component from the first container through the frangible seal into the second container, whereby substantially all is meant at least about 95%, usually at least about 97% and more usually at least about 99%.

Following introduction of the liquid component into the second container, the mixing means is then employed to thoroughly combine the two components in a manner such that substantially no unreacted components remain in the second container. In those embodiments where the mixing means comprises two grooved rollers which move in randomized fashion across the second container, the rollers will be moved across the second container a sufficient number of times to achieve substantially complete combination of the two components, where usually the number of times that the rollers are moved across the second container will range from about 40 to 120, usually from about 50 to 100 and more usually from about 60 to 90.

Following combination of the two components into the flowable product, the second movement means, e.g. the squeegee, is then actuated in a manner sufficient to move substantially all of the flowable product from the second container through the frangible barrier or seal into the third elongate container. Following preparation of the flowable product such that it is present in the third elongate member as described above, the lid of the device may then be opened and the storage means removed.

Also provided by the subject invention is a delivery device capable of delivering the flowable product present in the third compartment to site of interest, e.g. a physiological site of interest, such as a bone repair site. The delivery device of the subject invention comprises at least: (a) a holder for receiving an elongate container comprising a flowable material, i.e. the third elongate compartment from the storage means; (b) a means for substantially closing an open first end of the elongate container; (c) an exit port; and (d) an actuation means for moving the contents of the elongate container through the exit port.

The holder for receiving the elongate container has a sufficient volume for holding the container, where the volume may range in many embodiments from about 5 to 30 cc and usually from about 5 to 20 cc and will generally have a substantially circular cross sectional dimension. The device further comprises an opening means for introducing the elongate container into the holder, such as a removable lid which exposes the holder when moved to the open position.

When placed in the holder of the delivery device, the elongate container comprising the structural material will generally have an open first end. As such, the delivery device preferably comprises a means for substantially closing the open first end, where such means may be a clamp, sealing bar and the like, and may or may not be part of the actuation means which serves to move the contents of the elongate container through the exit port.

The actuation means is sufficient to move the flowable material, e.g. paste, from the interior of the elongate container present in the compartment out of the compartment through the exit port. While any convenient actuation means may be employed, in a preferred embodiment the actuation means comprises a roller or squeegee operably linked to a manually depressable handle which, upon depression of the handle moves along the container an a manner sufficient to force the contents of the container through the opening at the distal end of the compartment and out the exit port of the device. Alternatively, the device could comprise an automatic actuation means, such as a motorized pusher, that serves to force the contents of the container out of the device through the exit port.

The exit port of the device has dimensions sufficient for the fitment means of the container to at least partially extend outside of the device so that a tubular delivery means such as a needle, cannula or the like can be attached to the fitment means. As such the cross sectional area of the exit port will generally range from about 10 to 24 and usually from about 18 to 20 gauge, where the cross sectional shape will typically be designed to make a substantially close fit with the fitment means of the container.

Though not necessary, the elements of the delivery device described above are often present in a gun shaped housing which provides for easy manipulation of the device during use during administration of a the structural material to a bone repair site, as described in greater detail below.

In preparing the subject delivery device for use, the first step is to introduce the elongate container comprising the flowable structural material into the device compartment. This introduction step is accomplished by first pealing back the outer containment means of the storage means or package in a manner sufficient to expose substantially all of the elongate third container. The elongate third container is then separated from the remainder of the storage means, e.g. by cutting. Following separation, the elongate third container is then introduced into the compartment, e.g. by opening the lid of the gun shaped housing, exposing the compartment, and placing the container into the compartment. Following placement of the elongate container into the compartment, the lid, when present, is then closed, a tubular delivery means such as a needle or cannula is attached to the exposed sealing means of the container, the means is exposed through the exit port, and the actuation means is then activated to force or extrude the material out of the third container.

The subject system comprising the storage means, mixing device and delivery device of the invention having been generally described, each of these elements will now be discussed in greater detail in terms of the figures.

Turning now to the figures, as described above in general terms, the subject invention provides a system for the storage, preparation and delivery of a calcium phosphate cement, where system comprises storage means or disposable reactants pack 51, a mixing apparatus or mixer 52 and a delivery apparatus or device 53. Pack 51 is shown in detail in FIGS. 1–6 and includes an outer peelable package or pouch 56 and an inner package or mixing pouch 57 enclosed within the outer pouch 56. Inner pouch 57 has a first or rear end 57a and a second or front end 57b. Pouch 57 is formed from first and second flexible sheets 61 and 62 which are each rectangular in shape and have a length of approximately 9.5 inch and a width of approximately 3.75 inch. Sheets 61 and 62 are each substantially impervious to a liquid and are three layers in composition (see FIG. 2). Outer layer 66 is formed from a suitable polymeric material such as polyethylene terephthalate (PET), polyester or nylon having a thickness of 0.0005 inch. Intermediate or middle layer 67 is adhered to the outer layer 66 and is formed from a material capable of serving as a barrier to fluid and/or gaseous flow, such as aluminum foil having a thickness of approximately 0.0035 inch. Inner layer 68 is formed from polymeric material such as polyethylene having a thickness ranging from approximately 0.0025 to 0.0030 inch. The PET material of outer layer 66 provides strength and stiffness to sheets 61 and 62, while the aluminum foil material of middle layer 67 provides a moisture and gas barrier for preventing the fluids within pouch 57 from escaping and undesirable fluids from entering the pouch 57. The inert material of inner layer 68 prevents contamination of the materials within pouch 57 from sheets 61 and 62. Inner layer 68 also serves as heat seal means for securing together the abutting inner surfaces of sheets 61 and 62 at outer peripheries or margins 71 and forming an impervious seal at the margins 71.

Figure 2:
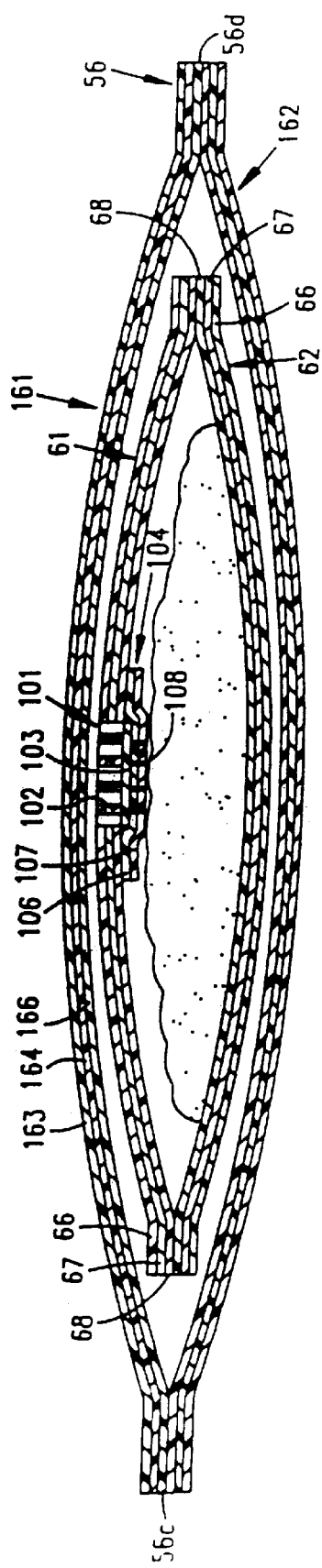
FIG. 2 is a cross-sectional view of the packet of FIG. 1 taken along the line 2—2 of FIG. 1.

First or second chambers or compartments 72 and 73 are provided within inner pouch 57 (see FIGS. 1 and 2). First and second sheets 61 and 62 are heat sealed transversely across the center thereof to provide a heat sealed strip 76 extending perpendicularly to the adjoined outer margins and forming compartments 72 and 73 with sheets 61 and 62. First or liquid compartment 72 is generally rectangular in shape and has a length of approximately 2.75 inches and a width of approximately 3.25 inches and comprises liquid component 83. Second or dry compartment 73 is substantially octagonal in shape and has a length at its longest point of approximately 5 inches and a width at its widest point of approximately 3.25 inches and comprises dry component 84. First and second sheets 61 and 62 are heat sealed together to provide first and second strips 81 which extend from outer margins 71 at opposite sides of inner pouch 57 toward internal strip 76 at an angle of approximately 35°. Similar first and second strips 82 extend from outer margin 71 toward the front end 57b of inner pouch 57 at an angle of approximately 40° to a point short of the midpoint of the front end 57b. As such, dry compartment 73 is generally free of 90° corners.

Figure 28:
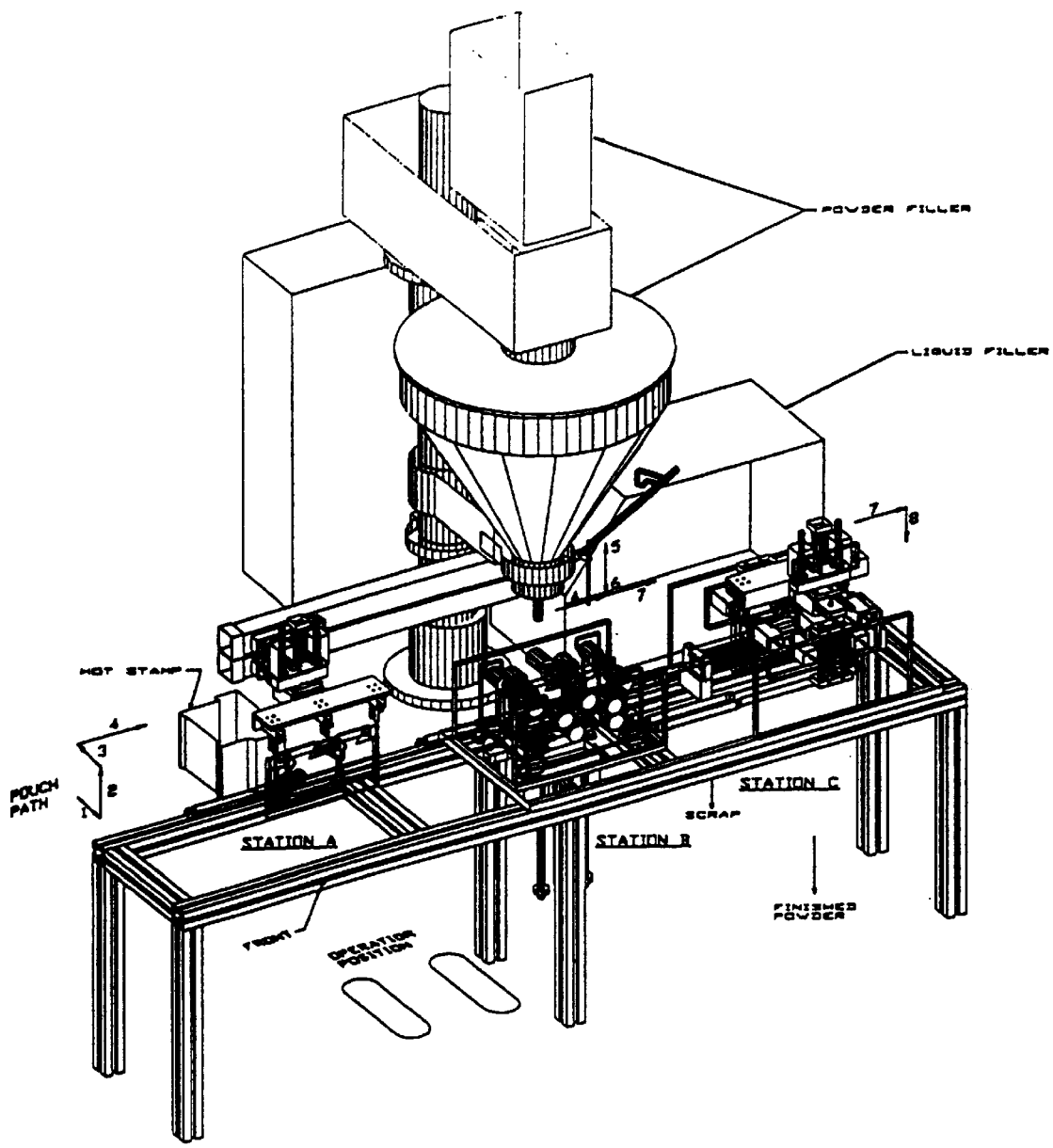
FIG. 28 is a representation of an automatic filling means for introducing dry and liquid components into the storage means shown in FIG. 1.

During the manufacture of inner pouch 57, ports 91 and 92 are provided in the otherwise heat sealed outer margin 71 to permit the introduction of liquid or lubricant 83 into liquid compartment 72 and powder 84 into dry compartment 73 (see FIG. 1). Ports 91 and 92 are subsequently heat sealed to enclose liquid 83 and powder 84 within inner pouch 57. A device suitable for automatically filling the compartments with the powder and liquid components is depicted in FIG. 28. The automatic filling device shown in FIG. 28 comprises a position for the operator to stand, a powder filler component, a liquid filler component, and a hot stamp component. The device works operatively to automatically fill and seal a storage means according to the subject invention. The portion 76a of internal seal strip 76 between the inner ends of strips 81 is formed with a peel strength ranging from approximately 0.5 to 3.0, usually 1.2 to 1.7 pounds per inch so as to be frangible at a pressure of greater psi to permit liquid 83 and powder 84 to be mixed together as described below. The remainder of the heat seals in pouch 57 have a peel strength ranging from approximately 1–3 pounds per inch. Frangible strip portion 76a has a length of approximately one inch.

A vent 101 is included within the means of inner pouch 57 for permitting gases but substantially no liquids to escape from dry compartment 73 during the mixing of liquid 83 and powder 84 (see FIGS. 1 and 2). Vent 101 is formed from a plurality of spaced-apart slits 102 extending through first sheet 61. A disc 103 made from a layer of any suitable hydrophobic material such as DURAPEL® by Millipore extends below slits 102. Disc 103 permits gas to flow therethrough at a rate of up to 40–50 l/min and has a water intrusion pressure of approximately 12 to 15 psi. Means which includes a bilaminate layer or cover 104 is provided for securing disc 103 to the inside of first sheet 61 around the periphery of slits 102. Cover 104 is formed with an upper layer 106 made from any suitable material such as polyethylene having a thickness of approximately 2 mils and a lower layer 107 made from any suitable material such as polyethylene having a thickness of approximately 0.002 inch. Cover 104 underlies disc 103 and has a circumference which engages and is heat sealed to inner layer 68 of inner pouch 57. A plurality of openings in the form of slits 108 are formed in cover 104. Slits 108 are preferably aligned in a averse direction corresponding to the direction of slits 102. It should be appreciated, however, that other forms of openings such as a plurality of pin holes can be provided and be within the scope of the present invention.

Figure 3:
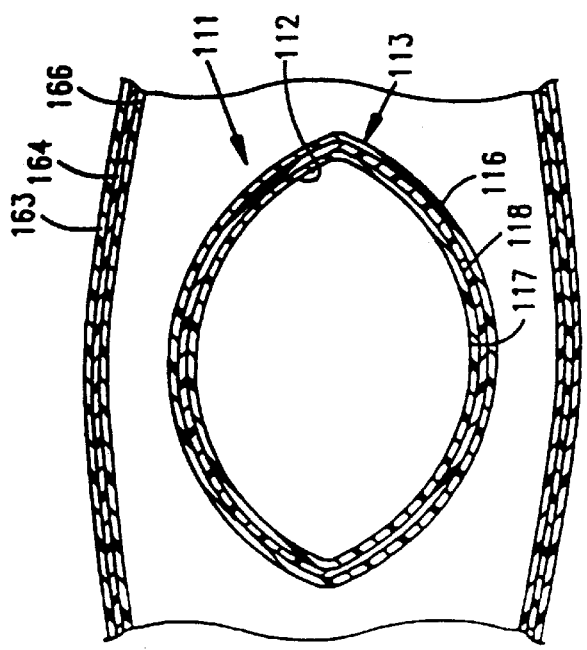
FIG. 3 is a fragmentary cross-sectional view of the packet of FIG. 1 taken along the line 3—3 of FIG. 1.

Inner pouch 57 further includes an elongate tubular member or delivery tube 111 having a first or rear end portion 111a and a second or front end portion 111b (see FIGS. 1 and 3). Tube 111 has a length of approximately eight inches and a diameter when made round of approximately ⅝ inch. The tube 111 can be extruded or blow molded and has an operating range of about 55 to 65 psi. A passageway or holding chamber 112 extends between end portions 111a and 111b and, as illustrated in FIG. 3, is formed from a thin wall 113 having a three layer structure. Holding chamber or delivery reservoir 112 is oblong in cross-section as shown in FIG. 3. Outer and inner layers 116 and 117 of thin wall 113 are each made from polyethylene and have a thickness ranging from 0.004 to 0.005 inch. Middle layer 118 is made from any suitable material such as Nylon and has a thickness ranging from 0.001 to 0.002 inch. Rear end portion 111a of the delivery tube extends between sheet outer margin 71 and is secured therein by any suitable means such as heat sealed strip 126 formed by sheets 61 and 62. A frangible seal 127 having a length of approximately one inch extends across the center of inner pouch 57 between the inner ends of heat seat strips 82. Frangible seal 127 is manufactured with a peel strength ranging from approximately 0.5 to 3.0, usually 1.2 to 1.7 pounds per inch so as to burst or open at a pressure of greater psi. The opening of seal 127 permits communication between mixing chamber 73 and holding chamber 112 of delivery tube 111. Substantially planar inner pouch 57 extends along a longitudinal axis 131 which passes through the center of the liquid and dry compartments 72 and 73 and holding chamber 112 of delivery tube 111 (see FIG. 1).

Figure 4:
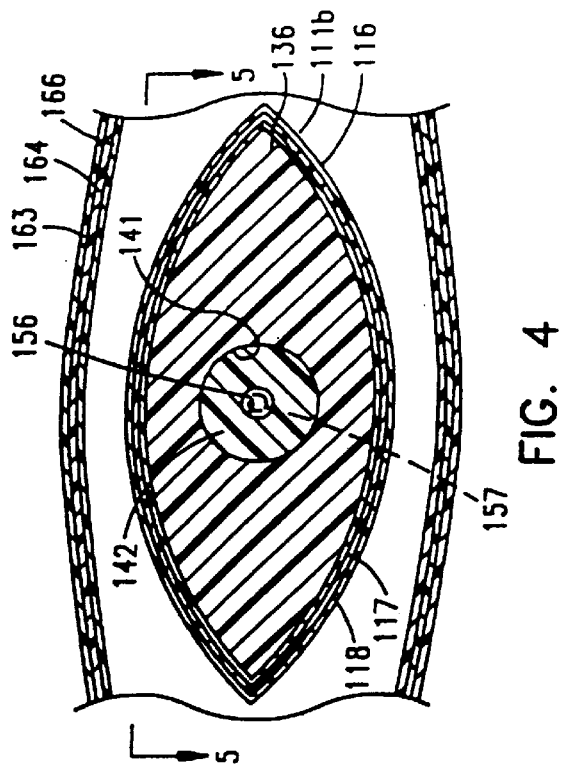
FIG. 4 is a fragmentary cross-sectional view of the packet of FIG. 1 taken along the line 4—4 of FIG. 1.
Figure 5:
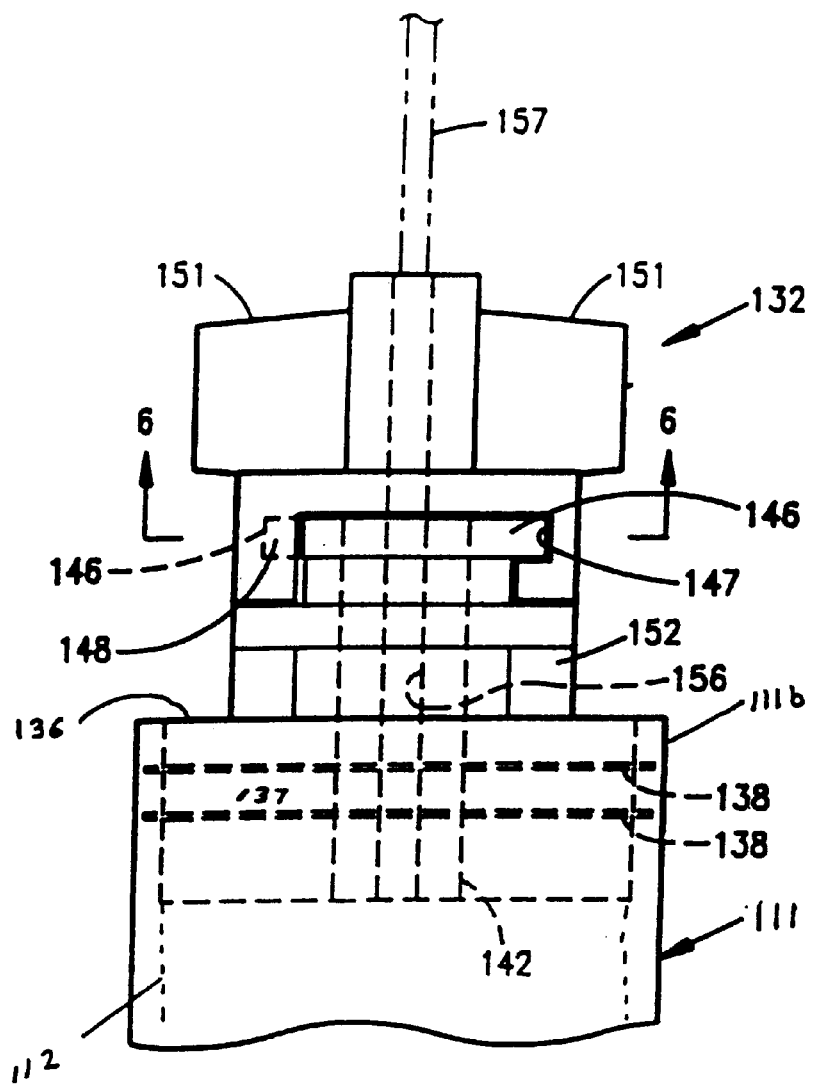
FIG. 5 is a top plan view of a portion of the packet of FIG. 1 taken along the line 5—5 of FIG. 4, with coupler 137 shown in solid lines.
Figure 6:
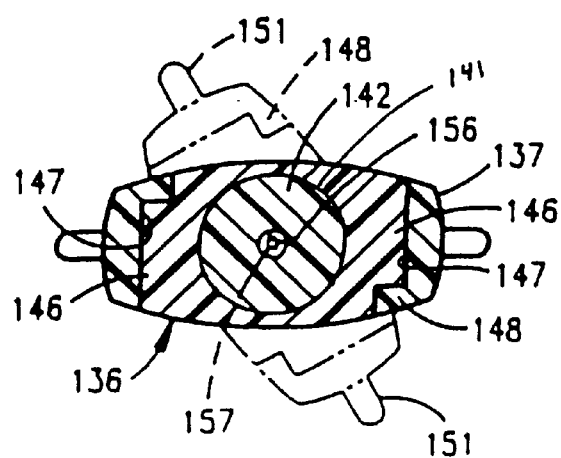
FIG. 6 is a cross-sectional view of the packet of FIG. 1 taken along the line 6—6 of FIG. 5.

Means consisting of fitment 136 is mounted on front end portion 111b of delivery tube 111 for permitting a delivery needle to be removably mounted to the delivery tube (see FIGS. 1, 4–6 and 34). Fitment 136 is made from any suitable material such as polyethylene and, as seen in FIGS. 5 and 6, has a shank portion which cooperatively mates with a coupling portion or coupler 132. As illustrated in FIGS. 4 and 5, the proximal extremity of the fitment has a cross section which is football-shaped and sized to fit within holding chamber 112. Delivery tube 111 is heat sealed or otherwise suitably secured about the proximal extremity of the fitment. First and second spaced-apart heat seal ribs 138 circumscribe fitment for improving the heat sealing process. A bore 141 extends longitudinally through the fitment for slidably and rotatably receiving cylindrical or bayonet portion 142 of coupler 132.

Cooperative mating means 146 is provided for locking coupler 132 to fitment 136 once bayonet portion 142 has been filly inserted and received within bore 141 (see FIGS. 5 and 6). Means 146 includes first and second diametrically-extending flanges formed on the distal end of fitment 136 and first and second diametrically-opposed recesses 147 formed on the proximal end of coupler 132 for receiving the flanges upon clockwise rotation of the coupler relative to the shank portion as shown in FIG. 6. Stops 148 formed on coupler 132 engage flanges 146 to limit the rotational locking of the coupler 132 to fitment 136 such that only a quarter turn is required to move the fitment to the "locked" position. First and second tabs or thumb wings 151 extend radially outwardly from opposite sides of the distal end of bayonet portion 142 for facilitating grasping of coupler 132 and the locking of the coupler to fitment 136. Fitment 136 has a central portion 152 of reduced thickness for registering within delivery device 53 as hereinafter described (see FIGS. 5 and 34). A central bore 156 extends through bayonet portion 142 of coupler 132 for receiving a needle 157 made from any suitable material such as stainless steel and having a passageway therethrough. Needle 157 is shown in phantom lines in FIGS. 5 and 6. Coupler 132 is shown in phantom lines in FIG. 1 because a fitment 136 can initially be provided on delivery tube 111 with no coupler 132. Alternatively, a coupler 132 with no needle 157 can initially be provided on the delivery tube 111.

Outer pouch 56 has a first or rear end 56a and second or forward end 56b and a first or left side 56c and second or right side 56d for forming the outer margin of the pouch (see FIG. 1). The outer pouch 56 is generally rectangular when viewed in plan and has a length of approximately 17.5 inches and a width of approximately 5 inches. At least one flexible sheet and as shown in FIGS. 2–4 first and second flexible sheets 161 and 162 are provided for forming outer pouch 56. Each of sheets 161 and 162 is substantially impervious to a liquid and has a three layer construction which includes an outer layer 163 made from PET with a thickness of approximately 0.0005 inch. A middle layer 164 made from silicon oxide is coated on the inside of outer layer 163 to reduce the permeability of outer pouch 56 and thus increase its shelf life. An inner layer 166 made from polyethylene with a thickness ranging from 0.0025 to 0.0030 inch is further provided, and may be made from a sealable polyethylene blend. It should be appreciated that middle layer 164 can be made from other materials such as aluminum foil and be within the scope of the present invention. It should be further appreciated that an outer pouch 56 having no intermediate layer can also be provided and be within the scope of the present invention. Where 166 is not fabricated from a sealable polyethylene blend, a layer of a heat sealable material is provided on surface of 166 to provide for a peelable heat seal.

A peelable heat seal 167 is included within the means for creating a sterile chamber 168 within first and second sheets 161 and 162. Heat seal 167 has a pull strength ranging from approximately 12–16 pounds per inch and extends generally around the outer margin of sheets 161 and 162 at rear end 56a and left and right sides 56c and 56d. The heat seal 167 has a portion 167a extending between sides 56c and 56d spaced from front end 56b and having the shape of a chevron. First and second sheets 161 and 162 extend beyond chevron portion 167a to form respective first and second flaps or pull tabs 171 and 172. The pull tabs 171 and 172 are secured together by heat seal tabs 173 at each of the two corners of outer pouch 56 adjoining front end 56b. Sterile chamber 168 is sized and shaped to receive inner pouch 57 therein. Chamber 168, and thus powder chamber 73, are evacuated prior to sealing of outer pouch 56. One semi-circular-shaped cutout 176 is provided in heat seal 167 along right side 56d and two longitudinally spaced-apart cutouts 177 are provided in heat seal 167 along left side 56d of the outer pouch 56.

Figure 7:
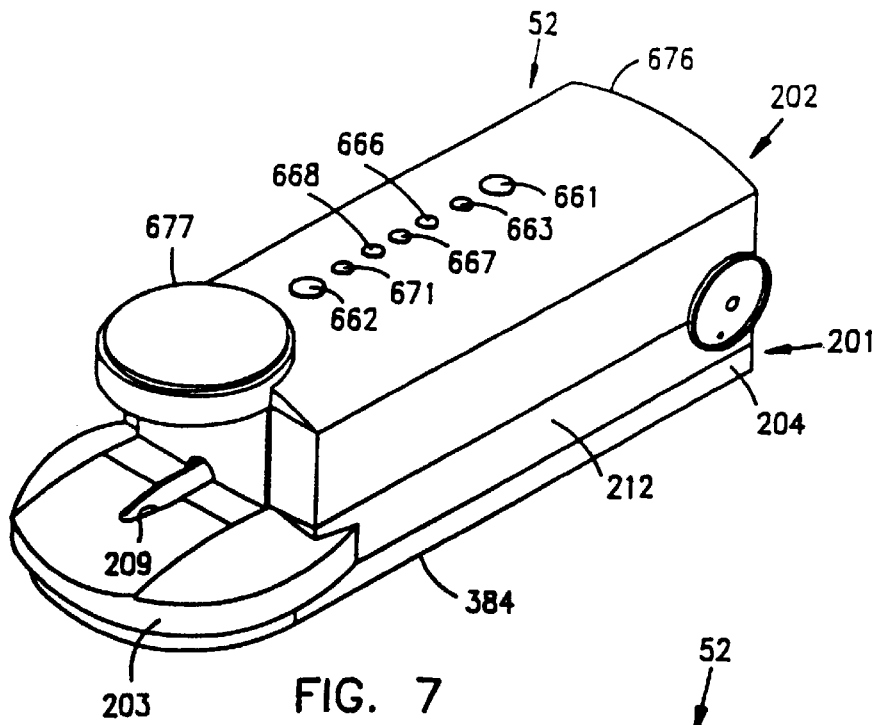
FIG. 7 is a perspective view of the apparatus of the present invention for mixing the contents of the packet of FIG. 1 in an operational position.

Mixer 52 is illustrated in FIGS. 7–27 and comprises a base member or base 201 and an upper portion or member 202. Base 201 is included within the framework of mixer 52 and is made from any suitable material such as aluminum. Base 201 is substantially rectangular in plan and has a front-end portion or lip 203 and a rear end portion or rear 204 (see FIGS. 7 and 8). A top horizontal surface 206 (FIG. 9) is provided and lip 203 slopes downwardly from the front end of top surface 206. First and second grooves 207 and 209 are formed in the top surface 206. First groove or channel 207 extends transversely across surface 206 and has a strip 208 made from silicone foam rubber or any other suitable material adhered along the center thereof. Groove 209 extends longitudinally through surface 206 and opens onto the forwardly sloping upper surface of lip 203. Left and right side portions which include left and right walls 211 and 212 extend upwardly from each side of surface 206. Left and right sets of posts 216 and 217 are further included within the left and right side portions of base 201. A left pin 218 extends transversely of the base 201 between left posts 216 and a similar right pin 219 extends transversely between the two right posts 217. Left and right upstanding disks 222 and 223 are formed integral with the rear 204 of base 201. Base 201 has a length between end portions of approximately 22 inches, a width between side portions of approximately seven inches and a height of approximately two inches.

Figure 8:
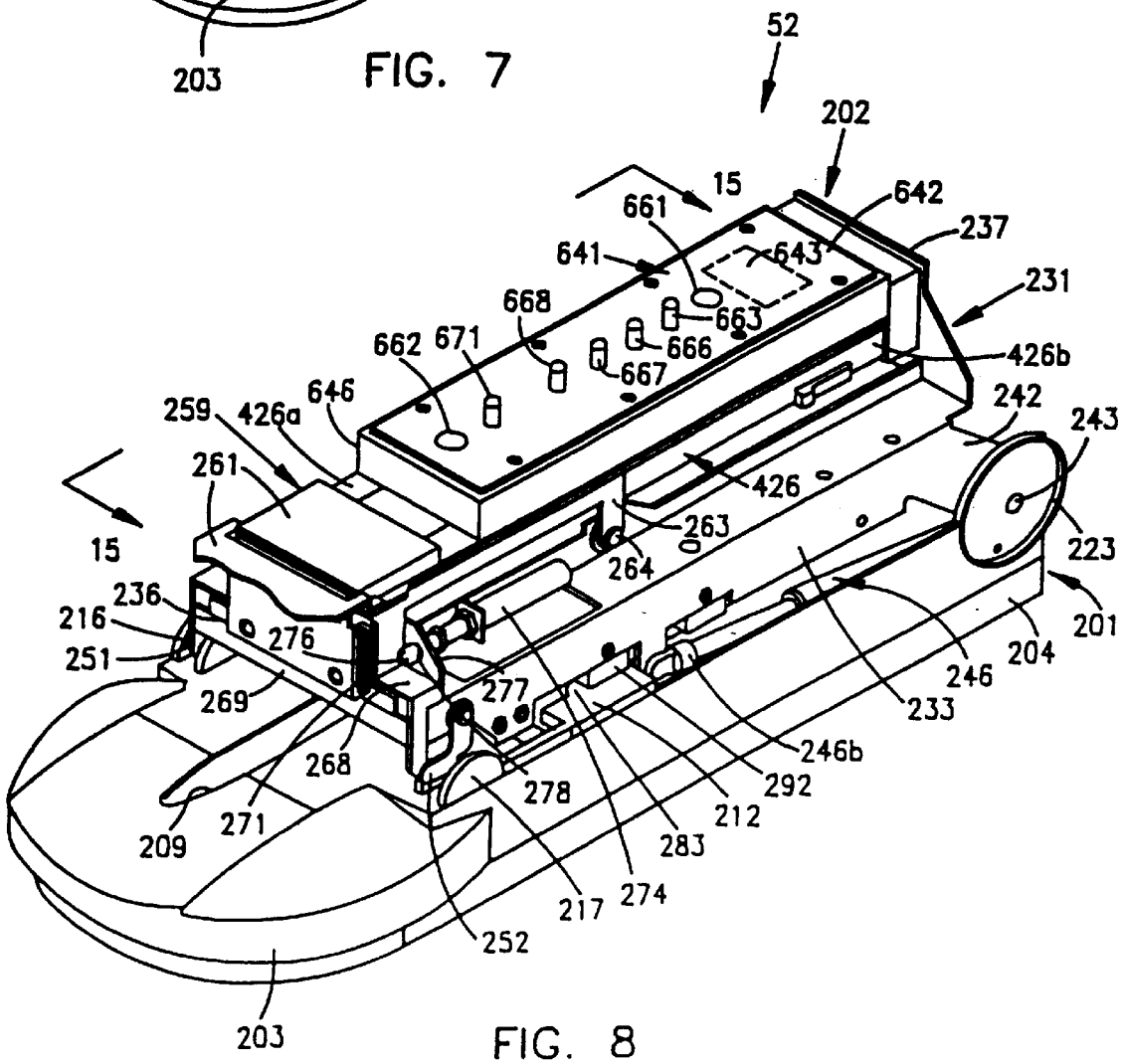
FIG. 8 is a perspective view, partially cut away, of the mixing apparatus of FIG. 7.
Figure 15:
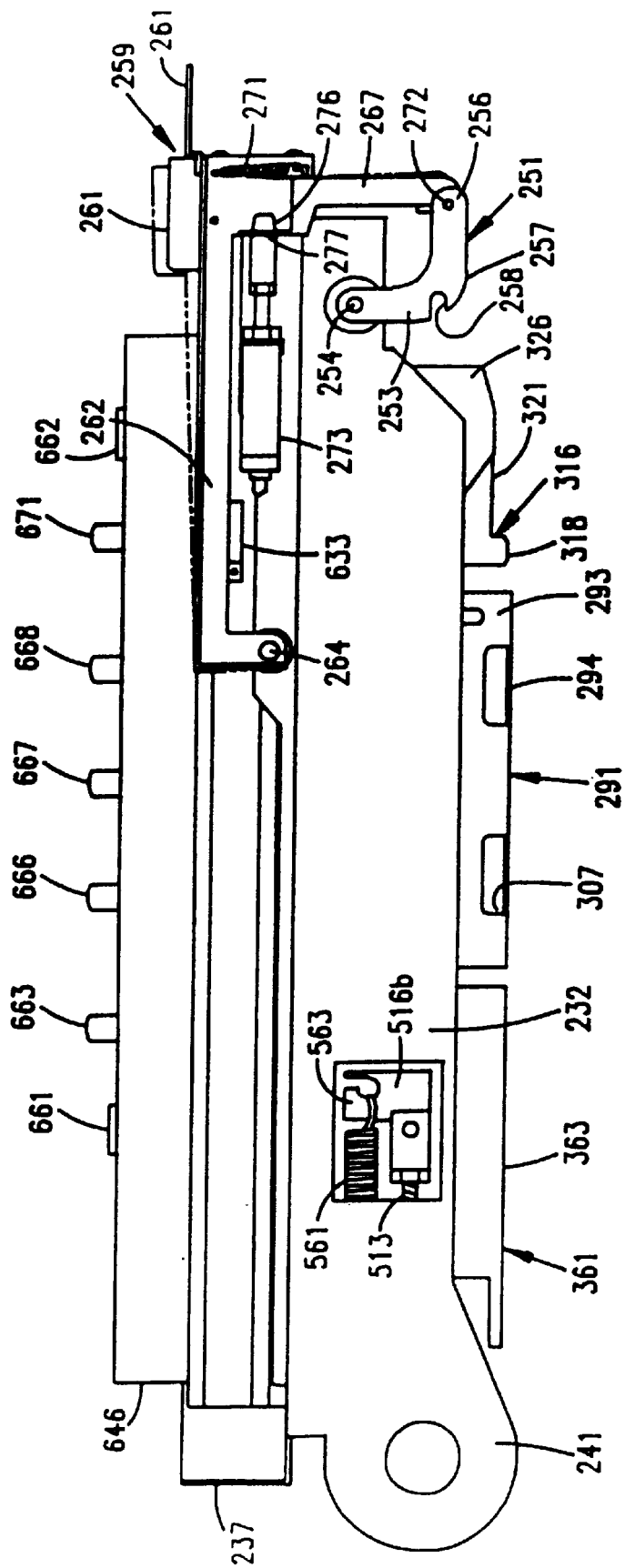
FIG. 15 is a side elevational view of a portion of the mixing apparatus of FIG. 7 taken along the line 15—15 of FIG. 8.

Upper portion or lid 202 includes a frame 231 and is included within the framework of mixer 52 (see FIGS. 8 and 15). Frame 231 includes left and right spaced-apart side members 232 and 233 and front and rear upstanding face plates 236 and 237 extending between the parallel side members 232 and 233. Left and right ears 241 and 242 angle rearwardly and downwardly from respective left and right members 232 and 233.

Figure 9:
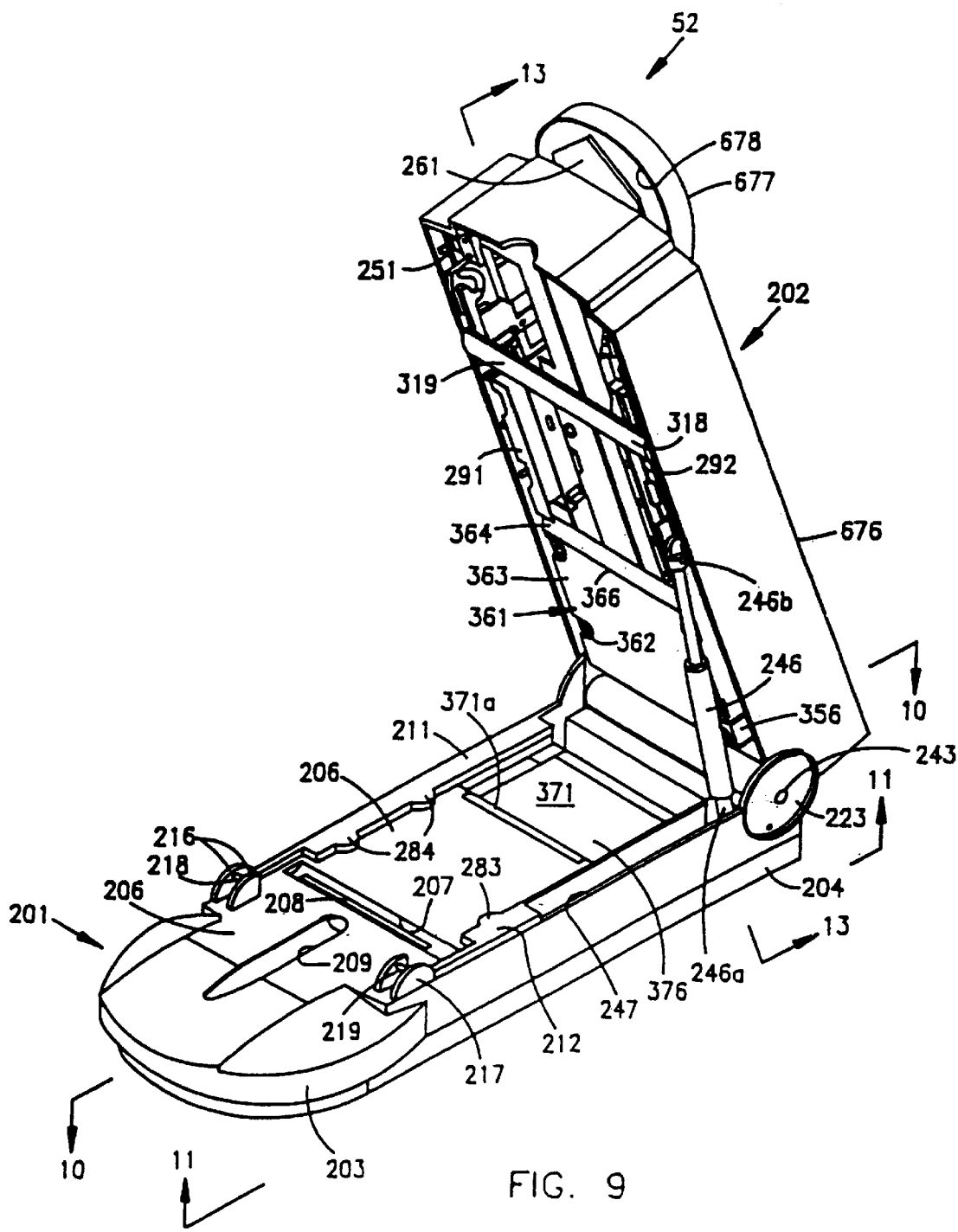
FIG. 9 is a perspective view of the mixing apparatus of FIG. 7 in an open position for inserting the packet of FIG. 1.

Lid 202 is pivotably mounted on base 201 (see FIGS. 8 and 9). In this regard, left and right ears 241 and 242 are juxtaposed along the inside of respective left and right disks 222 and 223 of base 201. A pivot pin 243 extends through the disks 222 and 223 and ears 241 and 242 along a transverse axis disposed at an approximately right angle to base walls 211 and 212. Lid 202 is thus pivotal about pin 243 between a first or closed position in which the lid substantially covers top surface 206, shown in FIGS. 7 and 8, and a second or open position in which the lid 202 extends at an angle of approximately 70° to base 201 and surface 206 thereof, shown in FIG. 9. A conventional gas spring 246 of the type known in the art is provided for supporting lid 202 in its open position. Gas spring 246 includes a first end portion 246a pivotably secured to base 201 by means of a pin and a second end portion 246b pivotably secured to frame 231 by means of another pin. Right wall 212 is provided with a recess 247 therein for receiving the gas spring 246.

Mixer 52 has means for keeping lid 202 in its closed position. As shown in FIGS. 8 and 15, this means includes left and right latches 251 and 252 secured to the front lower ends of respective left and right frame side members 232 and 233. Each of the latches 251 and 252 is made from stainless steel or any other suitable material and consists of an L-shaped member having an upstanding portion 253 pivotably coupled to frame 231 by a pin 254 and a forwardly-extending horizontal portion 256 disposed at a substantial right angle to upstanding portion 253. An arcuate surface 257 forms the outside corner between portions 253 and 256 and has a forwardly-extending slot 258 formed therein. Surfaces 257 engage and ride on left and right pins 218 and 216 when the lid 202 is moved to its horizontal position and cause latches 251 and 252 to pivot forwardly until the pins 218 and 216 enter slots 258.

Means is provided for releasing the latches 251 and 252 and consists of latch member 259 pivotably mounted to frame 231 (see FIGS. 8 and 15). Latch member 259 is made from stainless steel or any other suitable material and includes a horizontally-disposed top plate 261. A first or left pivot arm 262 and a second or right pivot arm 263 extend rearwardly from top plate 261 to respective left and right side members 232 and 233 of frame 231. A pivot pin 264 serves to pivotably couple the rear end of each pivot arm 262 to the frame side member 232 or 233. Thus, latch member 259 pivots about an axis extending transversely through pins 264 from a first or lower position shown in solid lines in FIG. 15 to a second or upper position shown in phantom lines in FIG. 15. Latch member 259 further includes a first or left latch arm 267 and a second or right latch arm 268 which depend from top plate 261. The latch arms are sized and shaped so as to extend around the sides of frame 231. A support bar 269 extends transversely below frame 231 between the lower ends of latch arms 267 and 268. The lower ends of left and right latch arms 267 and 268 are pivotably secured by left and right pins 271 to the front ends of respective left and right horizontal portions 256 of latches 251 and 252. In this manner, pivoting of latch member 259 to its upper position causes latches 251 and 252 to pivot upwardly and release from pins 218 and 219 of base 201. A tensioned coil spring 272 has atop end secured to latch member 259 and a bottom end secured to frame 231 for biasing the latch member 259 to its lower or locking position.

A first or left pneumatic piston assembly 273 and a second or right pneumatic piston assembly 274 are provided in mixer 52 as means for locking lid 202 in its closed position. The pneumatic assemblies 273 and 274 are mounted by any suitable means to respective left and right side members 232 and 233. Each of the assemblies 273 and 274 has a longitudinally-extending movable piston with a bullet 276 mounted on the end thereof. Latch member 259 has opposite left and right vertical plates 277 having respective bores 278 therein for receiving bullets 276. Plates 277 and bores 278 are aligned relative to pneumatic assemblies 273 and 274 so that as the rounded forward ends of bullets 276 enter and seat within bores 278, latch member 259 is urged to its lower or locking position. Bullets 276 and pneumatic assemblies 273 and 274 thus preclude latch member 259 from pivoting to its upper position for unlocking latches 251 and 252.

Figure 10:
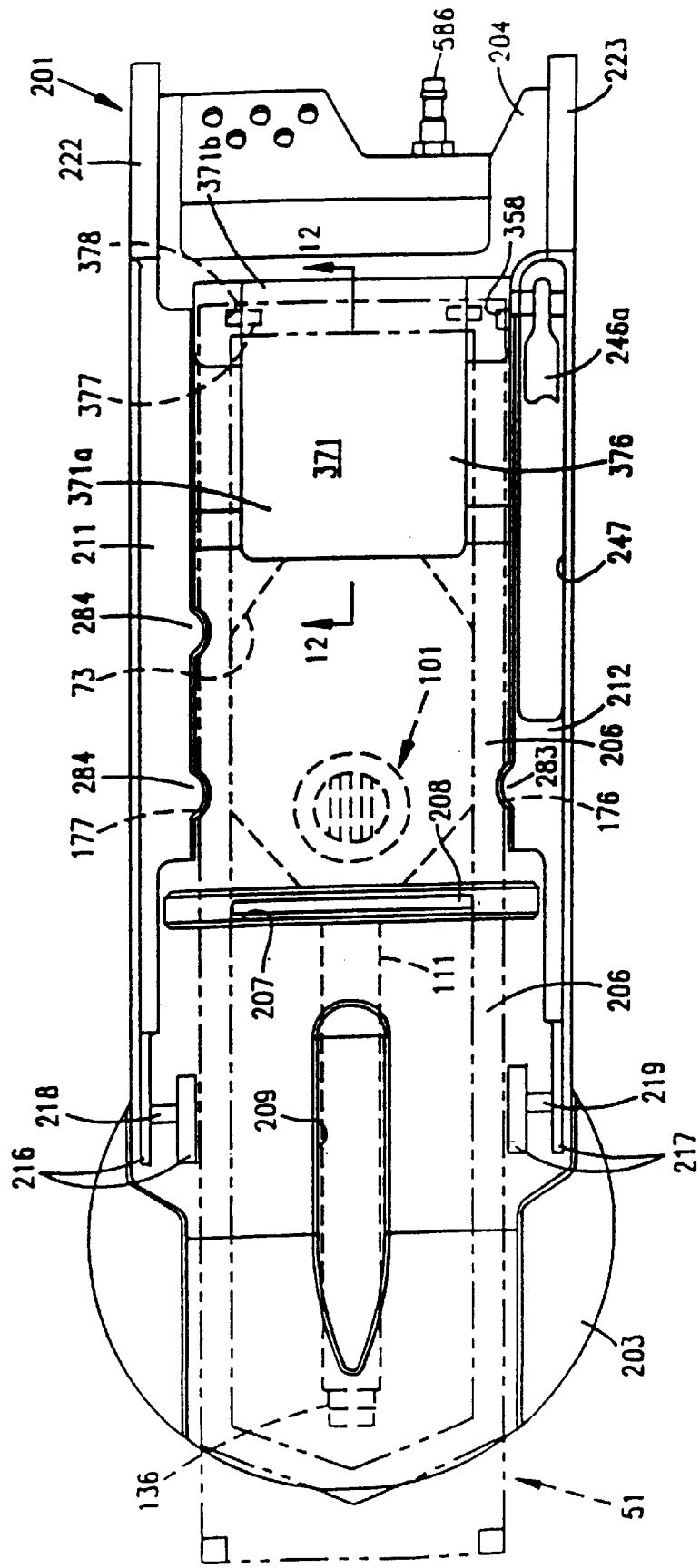
FIG. 10 is a top plan view of the base portion of the mixing apparatus of FIG. 7 taken along the line 10—10 of FIG. 9 with the packet of FIG. 1 shown thereon in phantom lines.

Pack 51 and base 201 are cooperatively sized and shaped so that the pack 51 can be placed within mixer 52 and lid 202 closed thereover (see FIG. 10). When pack 51 is disposed atop surface 206, transverse alignment between the pack 51 and the base 201 is achieved by the engagement of left and right sides 56c and 56d of the pack with left and right walls and left and right posts of the base. Longitudinal alignment is achieved by means of a transversely-extending protuberance 283 formed integral with the right wall and longitudinally spaced-apart similar protuberances 284 formed integral with the left wall. Protuberances or alignment protrusions 283 and 284 are positioned on the left and right walls so that they respectively engage cutouts 176 and 177 in pack 51 when frangible seal 127 is aligned over transverse channel 207 and vent 101 is facing upwardly. When the pack 51 is properly aligned on base 201, delivery tube 111 is received within longitudinal groove 209 and front end 56b of the pack drapes over and extends forwardly beyond lip 203.

Means for retaining pack 51 on base 201 and top surface 206 thereof includes first or left and second or right clamping members or package clamps 291 and 292 mounted on respective left and right frame side members 232 and 233 (see FIGS. 13–16). Clamps 291 and 292 are each made from stainless steel or any other suitable material. Each of the elongate clamps 291 and 292 includes a vertical portion 293 and a horizontal portion 294 disposed at a substantially right angle to the vertical portion so as to have a substantially L-shaped cross-section. Clamps 291 and 292 are attached to the inside of frame members 232 and 233 by means of left and right mounting blocks 296 and 297 secured to the frame 231 by bolts (not shown) or any other suitable means. Each of the blocks 296 and 297 is provided with a vertical slit 298 into which vertical portion 293 of the respective clamp 291 or 292 is disposed. The clamp 291 or 292 is vertically movable between a lower position shown in solid lines in FIGS. 16 and an upper position shown in phantom lines in FIG. 16. This vertical travel is guided by a plurality of transversely-extending pins 301 carried by block 296 or 297 and extending through respective vertical slots 302 provided in vertical portion 293. First and second spaced-apart spring means or springs 303 are carried within the mounting block 296 or 297 to engage the top of vertical portion 293. Springs 303 serve to urge the clamp 291 or 292 to its lower position. Upon closure of lid 202, horizontal portions 294 of left and right package clamps 291 and 292 engage left and right sides 56c and 56d of pack 51 to secure the pack against base 201. Vertical portions 203 generally abut left and right walls of the base. Right clamp 292 is provided with a cutout 306 and left clamp 291 is provided with longitudinally spaced-apart cutouts 307 for receiving respective protrusions 283 and 284 extending inwardly from walls of the base.

Clamping means in the form of burst seal clamping assembly 316 is carried by lid 202 for reinforcing the fluid-tight seal of tangible seal 127 during mixing (see FIGS. 13–16 and 25–26). Assembly 316 includes a burst seal clamp 317 made from stainless steel or any other suitable material and consisting of an elongate bar 318 extending perpendicularly between frame members 232 and 233. Bar 318 has a bottom surface 319 with a powder coated urethane finish thereon. First or left and second or right pivot arms 321 and 322 extend at right angles from the respective ends of bar 318. The ends of left and right pivot arms 321 and 322 are coupled to respective left and right side members 232 and 233 by means of left and right pins 323 disposed on an axis extending in a direction parallel to bar 318. Burst seal clamp 317 pivots through an angle of approximately 135° between a first or operational position shown in solid lines in FIGS. 13–16 and 25 and a second or released position shown in solid lines in FIG. 26. Bar 318 is seated within transverse channel 207 generally flush with base top surface 206 when burst seal clamp 317 is in its horizontal position and mixer 52 is closed. A helical spring 324 is coiled about each of the left and right pivot pins 323 and has one end 324a which extends around the respective pivot arm 321 or 322 to urge burst seal clamp 317 to its release position.

Figure 16:
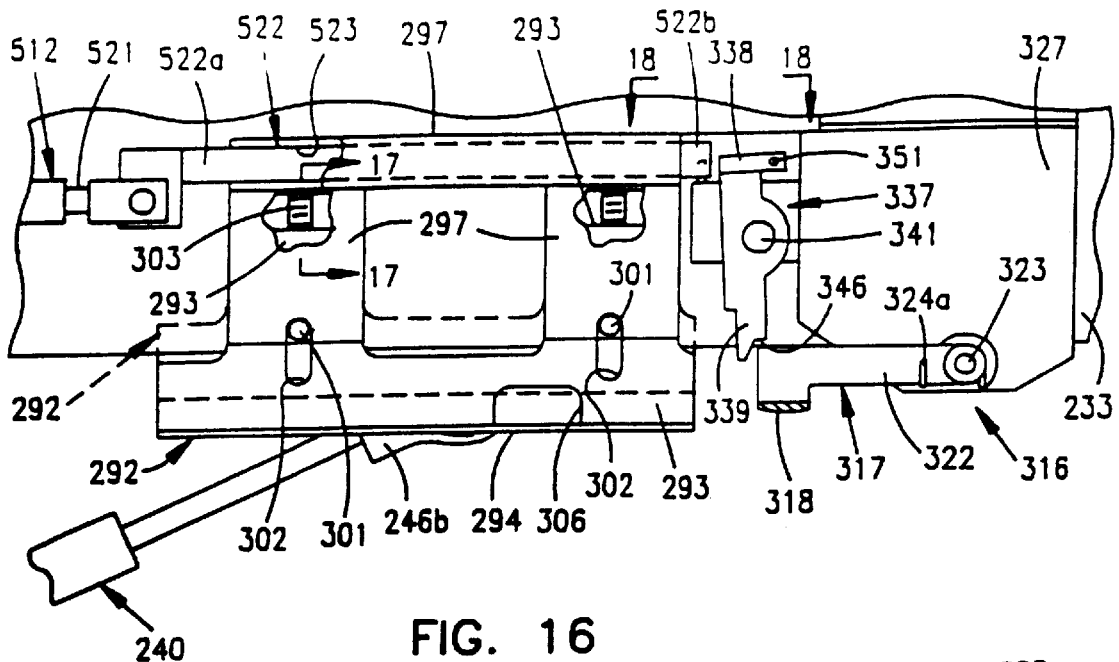
FIG. 16 is a fragmentary elevational view, partially cut away and rotated 180°, of a portion of the mixing apparatus of FIG. 7 taken along the line 16—16 of FIG. 14.
Figure 17:
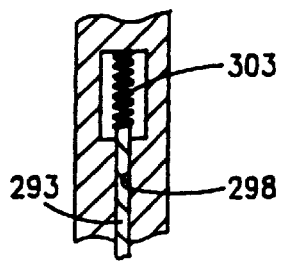
FIG. 17 is a fragmentary cross-sectional view of the mixing apparatus of FIG. 7 taken along the line 17—17 of FIG. 16.
Figure 18:
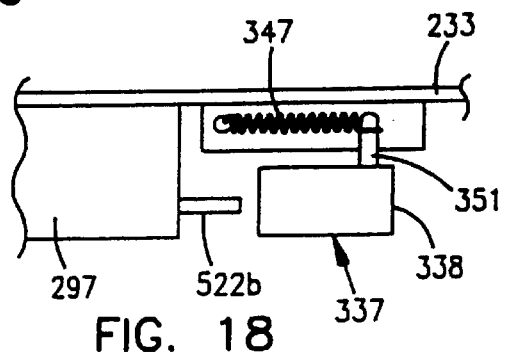
FIG. 18 is a fragmentary plan view of a portion of the mixing apparatus of FIG. 7 taken along the line 18—18 of FIG. 17.

First or left and second or right vertically-disposed blocks 326 and 327 are mounted to the inside of respective left and right side members 232 and 233 by any suitable means such as bolts (not shown) as shown in FIGS. 16, 25 and 26. As seen in FIGS. 25 and 26, left block 326 has an inner surface 331 provided with an arcuately-extending slot 332 having a constant radial dimension relative to left pin 323. Slot 332 receives a pin 333 extending perpendicularly outwardly from left pivot arm 321. Pin 333 serves to recock burst seal clamp 317 as discussed below.

Vertically-disposed first or left and second or right latches 336 and 337 are provided having respective upper end portions 338 and lower end portions 339 and a central hub portion therebetween for retaining clamp 317 in its horizontal position (see FIGS. 16, 25 and 26). Latches 336 and 337 are pivotally mounted to respective left and right side members 232 and 233 by means of left and right transversely-extending pivot pins 341. Each of pins 341 is secured to the side member at one end and pivotally mounted at its other end to the central hub portion of the latch 336 or 337. Lower end portions 339 are each provided with a cutout 346 for receiving the pivoting end of burst seal clamp arm 321 or 322. Left and right coil springs 347 are provided for rotatably urging latch upper end portions 338 rearwardly and thus latch lower end portions 339 forwardly against clamp arms 321 and 322 (see FIGS. 16–18). Each coil spring 347 extends longitudinally of mixer 52 and has a rear end coupled to respective side member 232 or 233 and a forward end coupled to a pin 351 extending transversely from latch upper end portion 338 toward the side member.

Figure 13:
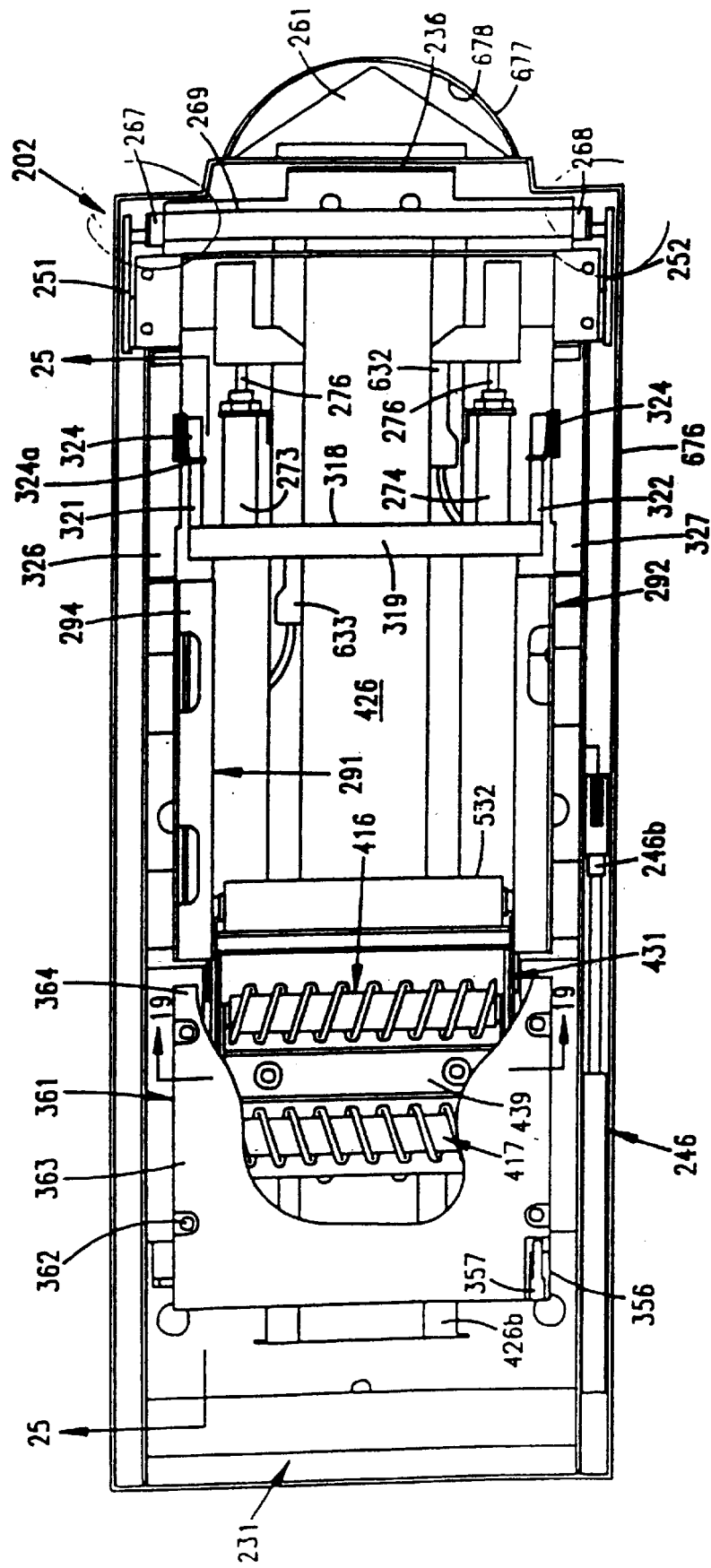
FIG. 13 is a bottom plan view, partially cut away, of the upper portion of the mixing apparatus of FIG. 7 taken along the line 13—13 of FIG. 9.
Figure 14:
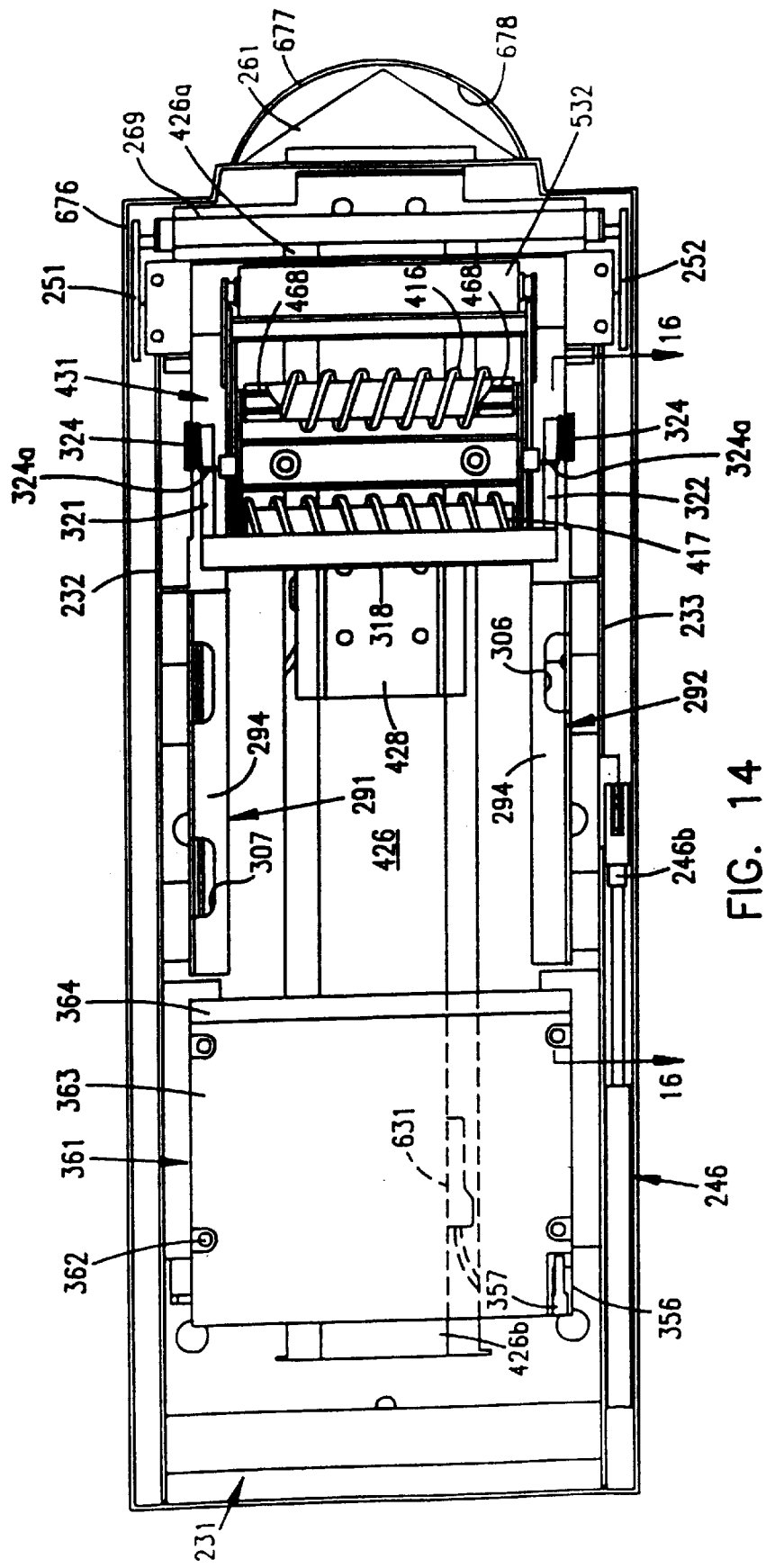
FIG. 14 is a bottom plan view, similar to FIG. 13 and partially cut away, showing the roller assembly of the upper portion of the mixing apparatus of FIG. 7 in another position.

A microswitch 356 is included within the means of mixer 52 for sensing whether a pack 51 is in place on base 201 when lid 202 is closed. As shown in FIGS. 9 and 13, microswitch 356 is mounted to the underside of lid 202 at the rear thereof. The microswitch 356 can be of any conventional type as known in the art, and includes a pivotable switch arm 357 extending downwardly therefrom. Base 201 is provided with a recess 358 at the rear thereof, as shown in FIG. 10, for receiving switch arm 357 when lid 202 is closed without a pack 51 on base surface 206. Switch 356 and recess 358 are latitudinally positioned on base 201 so that pack 51 extends therebetween when the pack 51 is properly positioned on base 201. As such, switch 356 engages the outer pouch 56 and pivots to a closed position when a pack 51 is placed within mixer 52.

Figure 11:
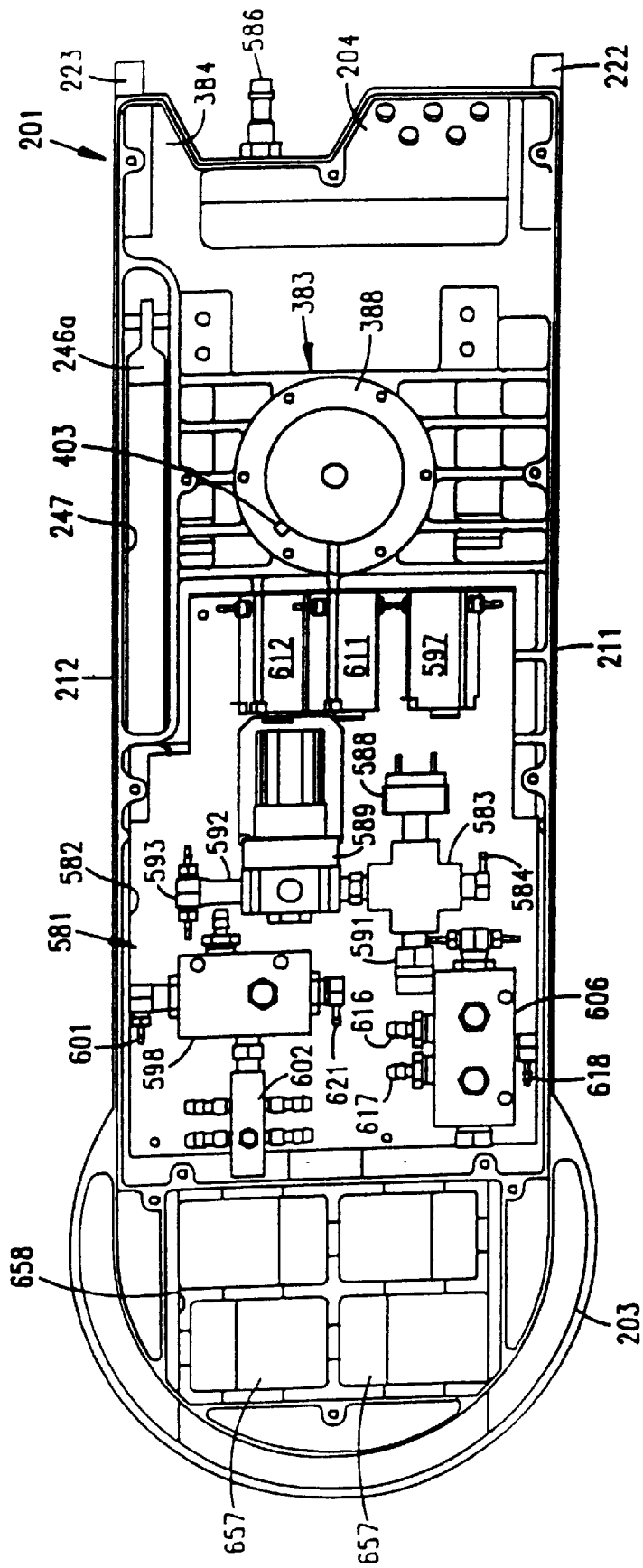
FIG. 11 is a bottom plan view of the base portion of the mixing apparatus of FIG. 7 taken along the line 11—11 of FIG. 9.
Figure 12:
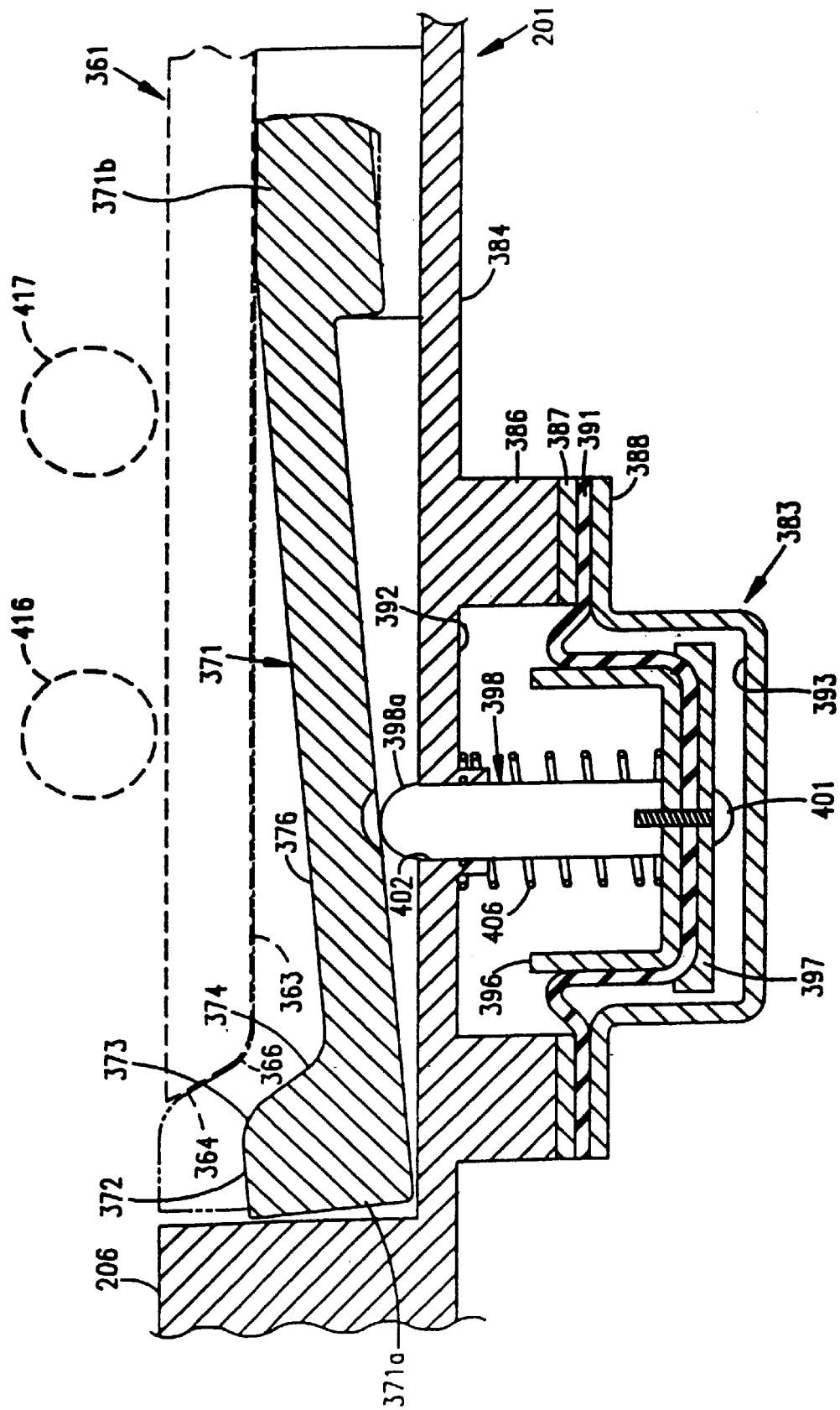
FIG. 12 is a fragmentary cross-sectional view of the mixing apparatus of FIG. 7 taken along the line 12—12 of FIG. 10.

Means is carried by the framework of mixer 52 for pressurizing liquid chamber 72 of pack 51 to break frangible seal portion 76*a* and for moving liquid 83 from the liquid chamber 72 into powder or mixing chamber 73 to mix with powder 84 therein (see FIGS. 9–14). This pressurizing and moving means includes a plate member or pressure plate 361 mounted in a horizontal position at the bottom rear of frame 231 by bolts 362 (see FIGS. 9, 13 and 14). Pressure plate 361 is made from aluminum or any other suitable material and is generally rectangular in plan. As best seen in FIG. 12, planar surface 363 forms the bottom of plate 361 and adjoins front end surface 364 at rounded corner 366.

A second plate member or pressure plate 371 is pivotally mounted to base 201 for abutting first pressure plate 361 (see FIGS. 10 and 12). Pressure or pivot plate 371 is made from aluminum or any other suitable material and is generally rectangular in plan. Pivot plate 371 has a front end portion in the form of upstanding ridge portion 371*a* and a rear end portion 371*b*. Ridge portion 371*a* is defined by a planar top surface 372 adjoining an outwardly rounded first corner 373 which in turn adjoins an inwardly rounded second corner 374. A planar surface 376 extends rearwardly from second corner 374 to end portion 371*b* of pivot plate 371. Left and right pins 377 extend transversely into the sides of plate rear end portion 371*b* for pivotably mounting the pivot plate to base 201. As shown most clearly in FIG. 10, each pin 377 is received in a bore 378 provided in the base 201. Pins 377 permit pivot plate 371 to move from a first or home position shown in solid lines in FIG. 12 to a second or clamping position shown in phantom lines in FIG. 12. In the home position, planar surface 376 extends at an angle of approximately 5° to bottom planar surface 363 of pressure plate 371. In the clamping position, second corner 374 and upper surface 376 of pivot plate 371 generally abut and are flush with lower surface 363 and rounded corner 366 of pressure plate 361.

Means in the form of pneumatic actuation assembly 383 is provided for moving pivot plate 371 from its home position to its clamping position (see FIGS. 11 and 12). Low profile actuation assembly 383 is carried by the underside 384 of base 201 and includes an annular wall 386 formed integral with the base. A ring 387 and a cup-shaped cap 388 disposed below ring 387 are mounted to annular wall 386 by any suitable means such as bolts. Ring and cap 387 and 388 are made form stainless steel any other suitable material. A diaphragm 391 made from rubber or any other suitable material has an outer periphery which extends between ring 387 and cap 388. Diaphragm 391 and annular wall 386 form a first or upper chamber 392 and diaphragm 391 and cap 388 form an airtight second or lower chamber 393. Diaphragm 391 is sandwiched within actuation assembly 383 between a cup 396 disposed in upper chamber 392 and a cap 397 disposed in lower chamber 393. Cup 396 and cap 397 provide the rigid support for a vertically-disposed piston 398 extending upwardly through the cup 396 and secured thereto by a bolt 401 extending sequentially through cap 397, diaphragm 391 and cup 396 into a threaded bore within the piston 398. Piston 398 has a rounded upper end 398*a* which extends through a bore 402 provided in base 201 so as to engage the underside of pivot plate 371. Cup 396, cap 397 and piston 398 are each made from stainless steel or any other suitable material. Cap 388 has a barb 403, shown in FIG. 11, which permits pressurized air to be introduced into lower chamber 393 and cause piston 398 to move upwardly and thus cause plate 371 to pivot upwardly against pressure plate 361. Piston 398 is biased downwardly by a helical spring 406 coaxially mounted about piston 398 and engaging base 201 at its top end and cup 396 at its bottom end.

Figure 19:
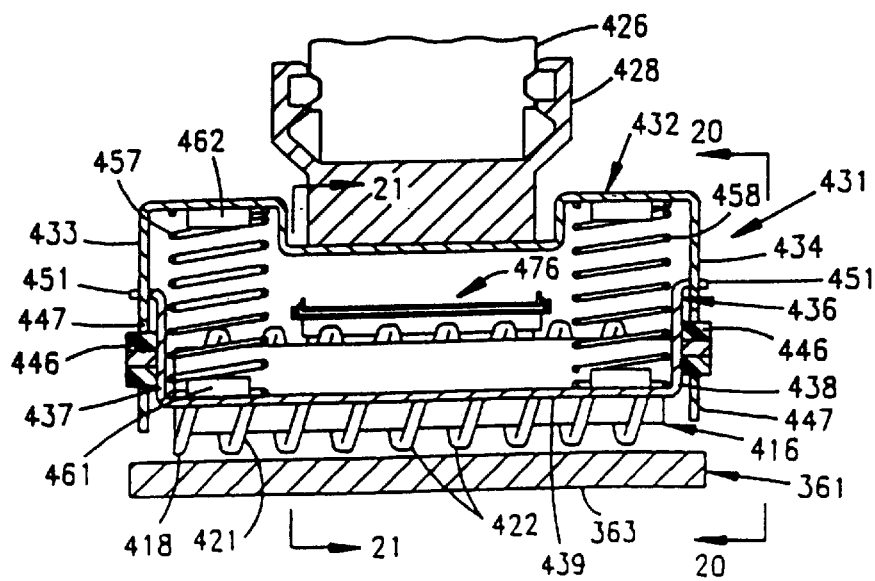
FIG. 19 is a fragmentary cross-sectional view, rotated 180°, of the roller assembly in the mixing apparatus of FIG. 7 taken along the line 19—19 of FIG. 13.

At least one roller and as shown a first or front roller 416 and a second or rear roller 417 are carried by lid 202 for movement back and forth across top surface 206 of base 201 and pack 51 disposed thereof (see FIGS. 13–14 and 19–21). Each of rollers 416 and 417 is made from plastic or any other suitable material and has a length at least equal to the width of powder chamber 73 and more specifically of approximately 3.5 inches and an outer diameter of approximately 0.75 inch. Rollers 416 and 417 are each formed with an outer cylindrical surface 418. At least one recess in the form of groove 421 extends around each of rollers 416 and 417 for forming at least one raised portion in the form of helical thread or land 422. Groove 421, as shown in FIG. 19, has a cross section between adjacent grooves 421 which is approximately U-shaped. The groove 421 has a depth of approximately 0.15 inch deep and width between adjacent lands 422 ranging from 0.125 to 0.250 inch and preferably approximately 0.125 inch. Land 422 has a pitch ranging from 0.4 to 0.5 inch and preferably approximately 0.5 inch. Front roller 416 is right-handed, that is helical land 422 of roller 416 advances in a clockwise direction, while rear roller 417 is left-handed, that is helical land 422 of roller 417 advances in a counter-clockwise direction (see FIGS. 13–14). Accordingly, the conformation of front and rear rollers 416 and 417 is different.

Means is provided for mounting front and rear rollers 416 and 417 to frame 231 and includes an elongate pneumatic or air cylinder 426 of a conventional type made by Lintra in Germany. Air cylinder 426 has front and rear portions 426a and 426b mounted respectively to front and rear face plates 236 and 237 by any suitable means such as bolts (not shown). Air cylinder 426 has a conventional slide bracket 428 slidably mounted along the bottom thereof.

A carriage assembly 431, shown in FIGS. 13, 14 and 19–21, is mounted to slide bracket 428 by bolts (not shown) or any other suitable means. Carriage assembly 431 includes an inverted U-shaped member or gull wing 432 having left and right depending side plates 433 and 434. A carriage member or roller carriage 436 extends between side plates 433 and 434 and has left and right end plates 437 and 438 and a U-shaped central portion 439 extending between plates 437 and 438. Gull wing 432 and roller carriage 436 are each made from stainless steel or any other suitable material. Vertically disposed end plates 437 and 438 are generally parallel with left and right side plates 433 and 434 and slidably abut the inside of the side plates 433 and 434.

Left and right slot bearings 446 extend aversely from the end plates 437 and 438 and are slidably received by respective left and right vertical slots 447 formed in left and right side plates 433 and 434 for permitting roller carriage 436 to move upwardly and downwardly with respect to gull wing 432. The slot or slide bearings 446 are made from plastic or any other suitable material and are rotatably mounted to respective left and right end plates 437 and 438 by bolts or any other suitable means. The upward and downward vertical travel of roller carriage 436 is limited by a pair of front and rear tab members or guides 451 and 452 formed integral with roller carriage 436 and extending upwardly and outwardly in longitudinally spaced-apart positions from each of the end plates 437 and 438 (see FIGS. 19 and 20). Tab members or guide tabs 451 and 452 extend respectively through first or front and second or rear openings 453 and 454 provided in each of side plates 433 and 434. The engagement of guide tabs 451 and 452 with the top of openings 453 and 454 limits the upward travel of roller carriage 436 relative to gull wing 432 and the engagement of the guide tabs with the lower edge of the openings limits the lower travel of the roller carriage. The roller carriage has a vertical travel with respect to gull wing 432 of approximately 0.4 inch.

Spring means in the form of first or left and second or right coil springs 457 and 458 are included within carriage assembly 431 for biasing or urging roller carriage 436 toward its lower position. The vertically disposed coil springs 457 and 458 engage the bottom of central portion 439 of roller carriage 436 adjacent respective left and right end plates 437 and 438. Retainer means in the form of left and right tubular retainers 461 extend upwardly into the coil springs for retaining the springs in position on roller carriage 436. The tops of coil springs 457 and 458 engage the inside of gull wing 432 adjacent left and right side plates 433 and 434 and are retained thereon by means of left and right tubular retainers 462 formed integral with the gull wing and extending downwardly to the coil springs.

Front and rear rollers 416 and 417 are rotatably mounted on carriage assembly 431 by means of respective front and rear shafts 468 and 469 secured at their ends to roller carriage 436. Shafts 468 and 469 extend along respective first and second parallel axes of rotation disposed on opposite sides of central portion 439, as shown in FIG. 13. Left and right conventional bearing assemblies are carried within each of rollers 416 and 417 and engage the opposite end portions of shafts 468 and 469 for facilitating the rotation of rollers 416 and 417 about the shafts 468 and 469. It should appreciated, however, that rollers 416 and 417 can be rotatably mounted on carriage assembly 431 without bearing assemblies and be within the scope of the present invention. As can be seen, roller carriage 436 permits front and rear rollers 416 and 417 to pivot about a first transverse axis extending through slide bearings 446 and a second axis extending longitudinally through carriage assembly 431 at a right angle to said first transverse axis.

Air cylinder 426 permits carriage assembly 431 and front and rear rollers 416 and 417 to move from a first or home position near the rear of air cylinder 426 to a second or intermediate position and then a third or forward position. In the home position, illustrated in FIG. 13, carriage assembly 431 is spaced above pressure plate 361 and rollers 416 and 417 are spaced above top surface 363 of the pressure plate a distance of approximately 0.10 inch. In the intermediate and forward positions, rollers 416 and 417 are positioned forward of transverse channel 207 and in engagement with top surface 206 of base 201. Front and rear guide tabs 451 and 452 are spaced above the bottom edge of respective front and rear openings 453 and 454 at distance of approximately 0.5 inch so that a force of at least 30 pounds is exerted by coil springs 457 and 458 on rollers 416 and 417 as they pass across surface 206.

Randomized relative angular rotation of front and rear rollers 416 and 417 is achieved in by the ability of the rollers to freewheel above pressure plate 361 as the rollers disengage top surface 206 during the rearward stroke of carriage assembly 431. The inclusion of bearing assemblies 468 within carriage assembly 431 facilitates this freewheeling. Accordingly, it should be appreciated that such an embodiment in which rollers 416 and 417 are spaced above pressure plate 361 or otherwise permitted to freewheel during mixing can be provided and be within the scope of the present invention.

Means is included within mixer 52 for releasing left and right latches 336 and 337 so as to cause burst seal clamp 317 to move from its operational position, in which bar 318 is seated within transverse channel 207, to its out-of-the-way position, shown in FIG. 26. The release means includes left and right pneumatic actuation cylinders 511 and 512 mounted to the inside of respective left and right side members 232 and 233 of frame 231. As illustrated in FIGS. 13, 15 and 25–26, left actuation cylinder 511 includes a piston 513 which moves from a retracted position shown in FIG. 25 to an extended position shown in FIG. 26. A left plate member or slide plate 516 made from stainless steel or any other suitable material is slidably mounted on the inside of left mounting block 296. Mounting block 296 has an inwardly extending pin 517 and slide plate or shifter 516 has a longitudinally-extending slot 518 for forming pin and slot means to permit left shifter 516 to move from a first or rear longitudinal position shown in FIG. 25 to a second or forward longitudinal position shown in FIG. 26. Left shifter 516 has a rear end portion 516a attached to piston 513 and a front end portion 516b which engages and pivots upper end portion 338 of left latch 336 to thus release left pivot arm 321 of burst seal clamp 317.

Right actuation cylinder 512 is substantially similar to left actuation cylinder 511 and includes a longitudinally movable piston 521 (see FIG. 16). A right plate member or side plate 522 is longitudinally disposed for slidable movement in a passageway 523 provided in right mounting block 297. Right slide plate or shifter 522 has a rear end portion 522a attached to piston 521 and a forward end portion that protrudes beyond the forward end of mounting block 297 for engagement with upper end portion 338 of right latch 337. Right actuation cylinder 512 and right shifter 522 thus serve to pivot right latch 337 so as to release right pivot arm 322 of burst seal clamp 317 simultaneously with the release of left pivot arm 321.

Figure 20:
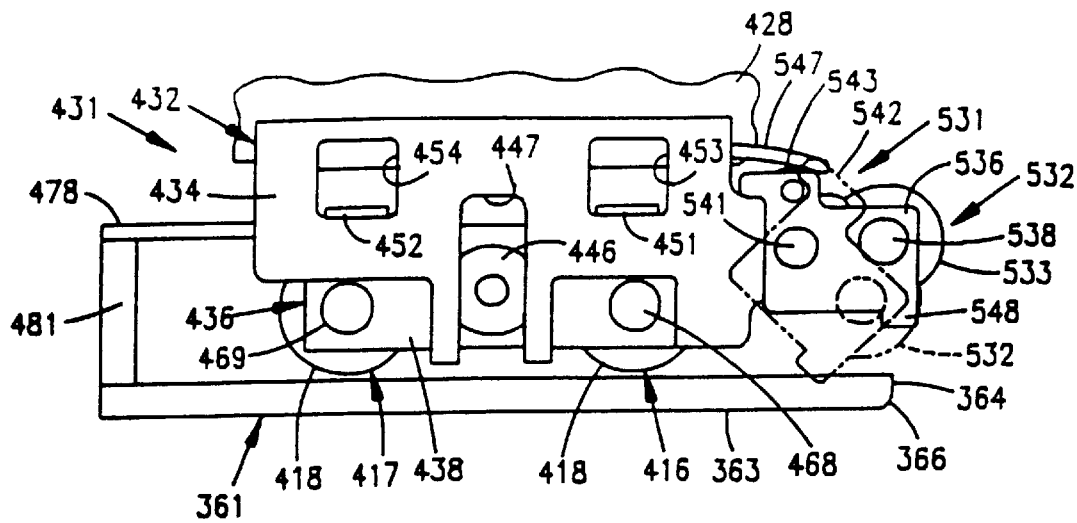
FIG. 20 is a fragmentary elevational view of the roller assembly in the mixing apparatus of FIG. 7 taken along the line 20—20 of FIG. 19.
Figure 21:
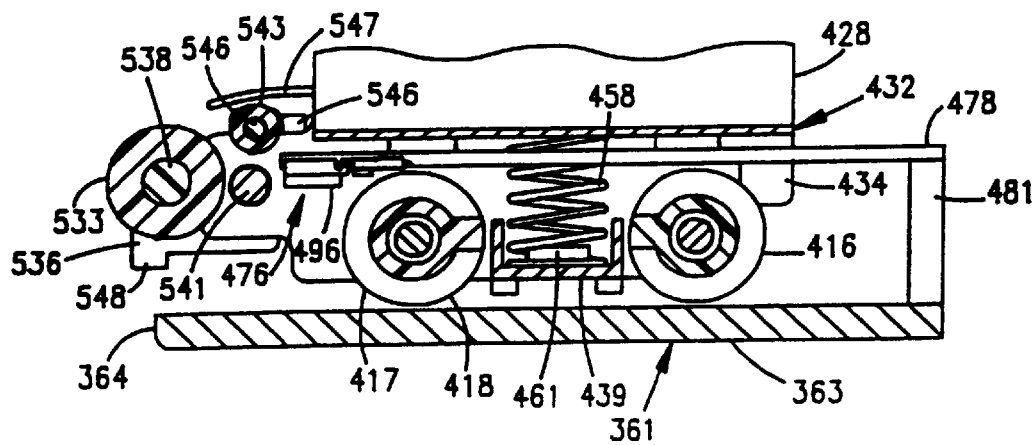
FIG. 21 is a fragmentary cross-sectional view of the roller assembly in the mixing apparatus of FIG. 7 taken along the line 21—21 of FIG. 19.
Figure 22:
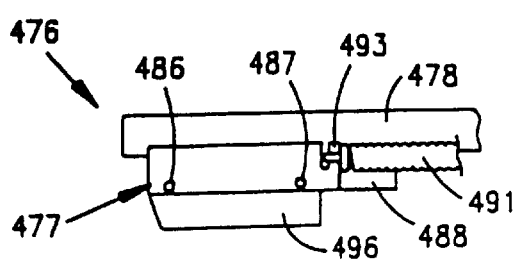
FIG. 22 is an enlarged fragmentary view of a portion of the roller assembly in the mixing apparatus of FIG. 7 shown in FIG. 21.
Figure 23:
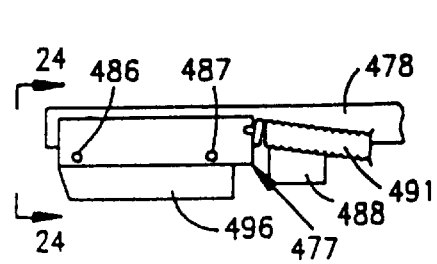
FIG. 23 is an enlarged fragmentary view, similar to FIG. 22, of the roller assembly in the mixing apparatus of FIG. 7 in another position.
Figure 24:
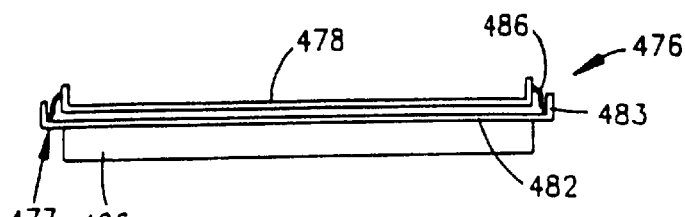
FIG. 24 is a front elevational view of a portion of the roller assembly in the mixing apparatus of FIG. 7 taken along the line 24—24 of FIG. 23.

Means in the form of squeegee assembly 531 is included within mixer 52 for pressurizing powder chamber 73 so as to burst frangible seal 127 (see FIGS. 13–14 and 20–21). Squeegee assembly 531 further serves to move the material within powder chamber 73 through the burst seal 127 into holding chamber 112 of delivery tube 111. The assembly 531 includes a squeegee roller 532 made from any suitable elastomer such as neoprene® having a durometer ranging from 50 to 60 Shore A. Squeegee roller 532 has an outer cylindrical surface 533 and is transversely mounted at its left and right ends to respective left and right pivot plates 536 by means of shaft 538. Left and right pivot plates 536, made from SST or any other suitable material, are in turn pivotally mounted to respective left and right side plates 433 and 434 of gull wing 432 by respective pins 541. Squeegee roller 532 thus rotates about an axis of rotation extending parallel to the axes of rotation of front and rear rollers 416 and 417. The squeegee roller 532 also pivots about a transversely-extending axis defined by pins 541 between a first or upper out-of-the-way position shown in solid lines in FIG. 20 and a second or operational position shown in phantom lines in FIG. 20. When mixer 52 is closed and pivot plates 536 are pivoted downwardly, squeegee roller 532 is elevationally positioned so as to engage top surface 206 as carriage assembly 431 passes over base 201. Pivot plates 536 are each formed with an upstanding portion 542 between which an additional roller 543 is rotatably mounted by means of pins 546. A leaf spring 547 is mounted to the underside of gull wing 432 and extends forwardly to engage the transversely extending roller 543 to retain squeegee roller 532 in its out of the way position. The left pivot plate 536 is further formed with a depending portion 548 as shown in FIG. 20.

Left actuation cylinder 511 and shifter 516 also serve as means for pivoting squeegee roller 532 from its out-of-the-way position to its operational position. In this regard and as shown in FIGS. 25–27, left shifter 516 includes an inwardly extending tab 555 formed integral with rear end portion 516a thereof. Tab 555 is sized so as to engage upstanding portion 542 of left pivot plate 536 as shifter 516 moves longitudinally forward under the force of actuation cylinder 511. Left pivot plate 536 is shown in phantom lines in FIG. 25 prior to it being contacted by tab 555 and in phantom lines in FIG. 26 after it has been pivoted forwardly by the tab 555.

Spring means in the form of helical tension spring 561 is included within mixer 52 for recocking left shifter 516 and burst seal clamp 317 (see FIGS. 15 and 25–26). The rear end of longitudinally-extending spring 561 is attached to the inside of left side member 232 and the front end of spring 561 is attached to a hook 563 formed on rear end portion 516a of left shifter 516. Tension spring 561 exerts a continual rearward force on left shifter 516. As such, the tension spring 561 causes the shifter 516 to move back to its rear position shown in FIG. 25 once left actuation cylinder 511 is deactivated.

A bell crank member or bell crank 566 is pivotally mounted to the inside of left side member 232 by means of pin 567 for returning squeegee roller 532 from its operational position to its out-of-the-way position during the final return stroke of carriage assembly 431 (see FIGS. 25 and 26). Bell crank 566 is made from stainless steel or any other suitable material and includes first and second arms 568 and 569 joined at an acute angle. Pin 567 is coupled to second arm 569 where the arm 569 joins first arm 568 and permits bell crank 566 to pivot between a first or home position shown in FIG. 26 and a second or operational position shown in FIG. 25. A helical tension spring 571 is joined at its front end to the apex of bell crank 566 below pin 567 and at its rear end to frame side member 232 so as to urge the bell crank to its home position. Left shifter 516 engages the vertically-inclined second arm 569 during its return stroke to pivot bell crank 566 to its operational position and thus cause first arm 568 to angle upwardly from the horizontal. A stop in the form of a transversely extending pin 572 is provided at the free end of first arm 568 for engaging the depending portion 548 of left pivot plate 536 and thus cause squeegee roller 532 to pivot back to its out-of-the-way position shown in solid lines in FIG. 20.

An elongate member or bar 576 extends behind left block 326 and left mounting block 296 for coupling burst seal clamp 317 to shifter 516 (see FIGS. 25–26). Strip-like bar 576 is made from stainless steel or any other suitable material. Specifically, the front end of bar 576 is attached to pin 333 and the rear end of the bar 576 is attached to an additional pin 577 extending through left mounting block 296 and attached to shifter 516 for slidable movement therewith. Thus, the rearward movement of left shifter 516 causes pin 333 to move through slot 332 and burst seal clamp 317 to pivot rearwardly about pins 323 to its operational position shown in FIG. 25.

Mixer 52 has been described in terms of a pneumatic actuation means that serves to actuate the various elements of the device described above. The pneumatic actuation means employed is conventional in nature and readily producible by those of skill in the art and has therefore not be shown in greater detail. As described above, the actuation means can also be an electronic actuation means of the type known to those of skill in the art. The device can be started and stopped using a convention on/off switch.

Delivery device 53, illustrated in FIGS. 29–34, has a support structure which includes a housing or shell 701 made from any suitable material such as aluminum or plastic. Housing 701 has an elongate upper portion 702 which is generally cylindrical in shape and has front and rear ends 702a and 702b (see FIG. 29). A top half 703 is pivotally coupled to a bottom half 704 at rear end 702b by means of a pin 706. Housing 701 further includes handle means in the form of handle portion or handle 707 which depends from upper portion 702.

Upper portion 702 forms an elongate internal chamber or compartment 711 having a platform 712 extending forwardly therein along a longitudinal axis from handle 707 to front end 702. Platform 712 has opposite upper and lower planar surfaces 713 and 714 (see FIGS. 30–31). Upper portion 702 is adapted to receive delivery tube 111 having therein the biocompatible hydraulic calcium phosphate cement composition 716 prepared by mixer 52. In this regard, platform 712 has a length and width at least equal to the length and width of delivery tube 111. Clamping means 718 is provided at front end 702a of upper portion 702 to receive and secure to device 53 the coupler 132 provided at front end portion 111b of the delivery tube (see FIG. 34). The clamping means 718 includes upper and lower lips 721 and 722 formed in respective top and bottom halves 703 and 704 of housing 701. The lips 721 and 722 have respective recesses 723 and 724 therein which, together, form an opening in housing 701 which is sized and shaped to cooperatively receive central portion 152 of fitment 132 with a snug fit. Lips 721 and 722 thus preclude longitudinal movement of delivery tube 111 relative to delivery device 53.

Figure 32:
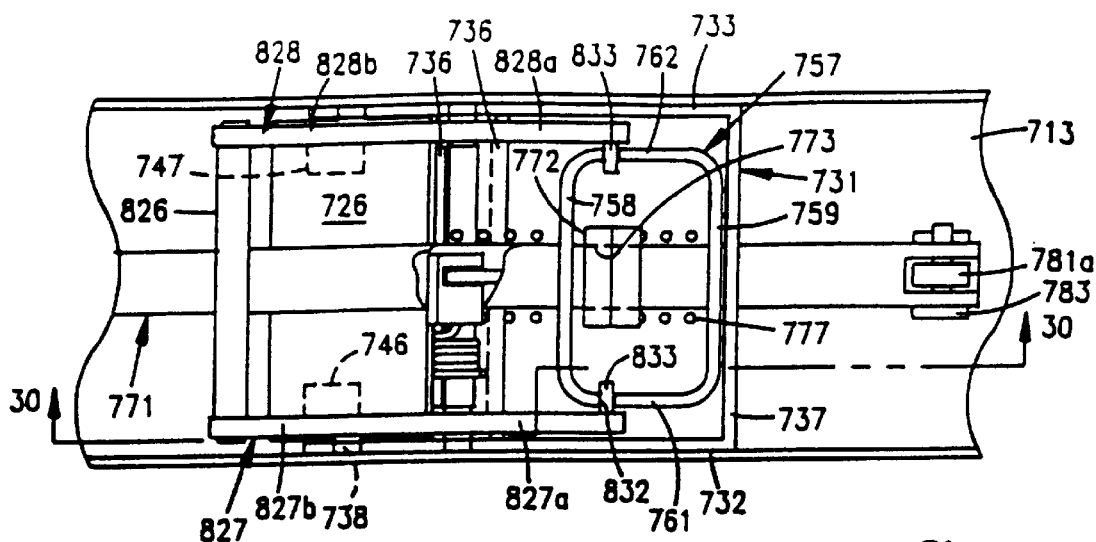
FIG. 32 is a fragmentary plan view of a portion of the delivery apparatus of FIG. 29 taken along the line 32—32 of FIG. 30.
Figure 29:
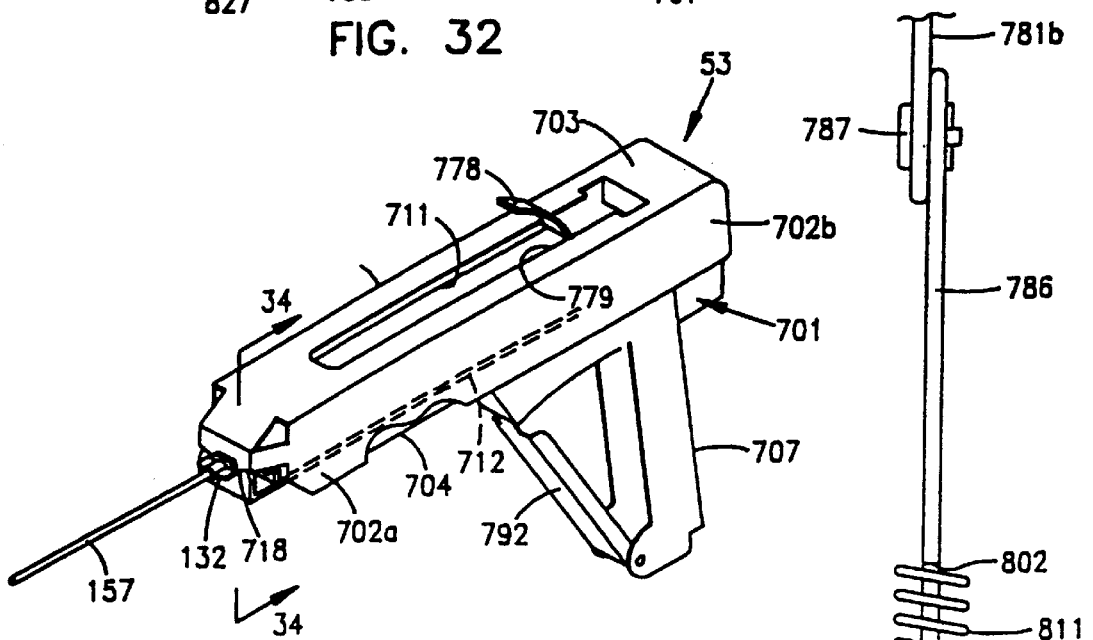
FIG. 29 is a perspective view, partially cut away, of the apparatus of the present invention for delivering the contents of the packet of FIG. 1.
Figure 34:
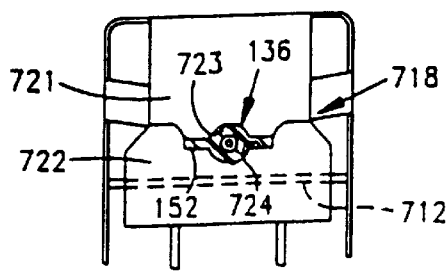
FIG. 34 is an end on view of the delivery apparatus of FIG. 29.
Figure 30:
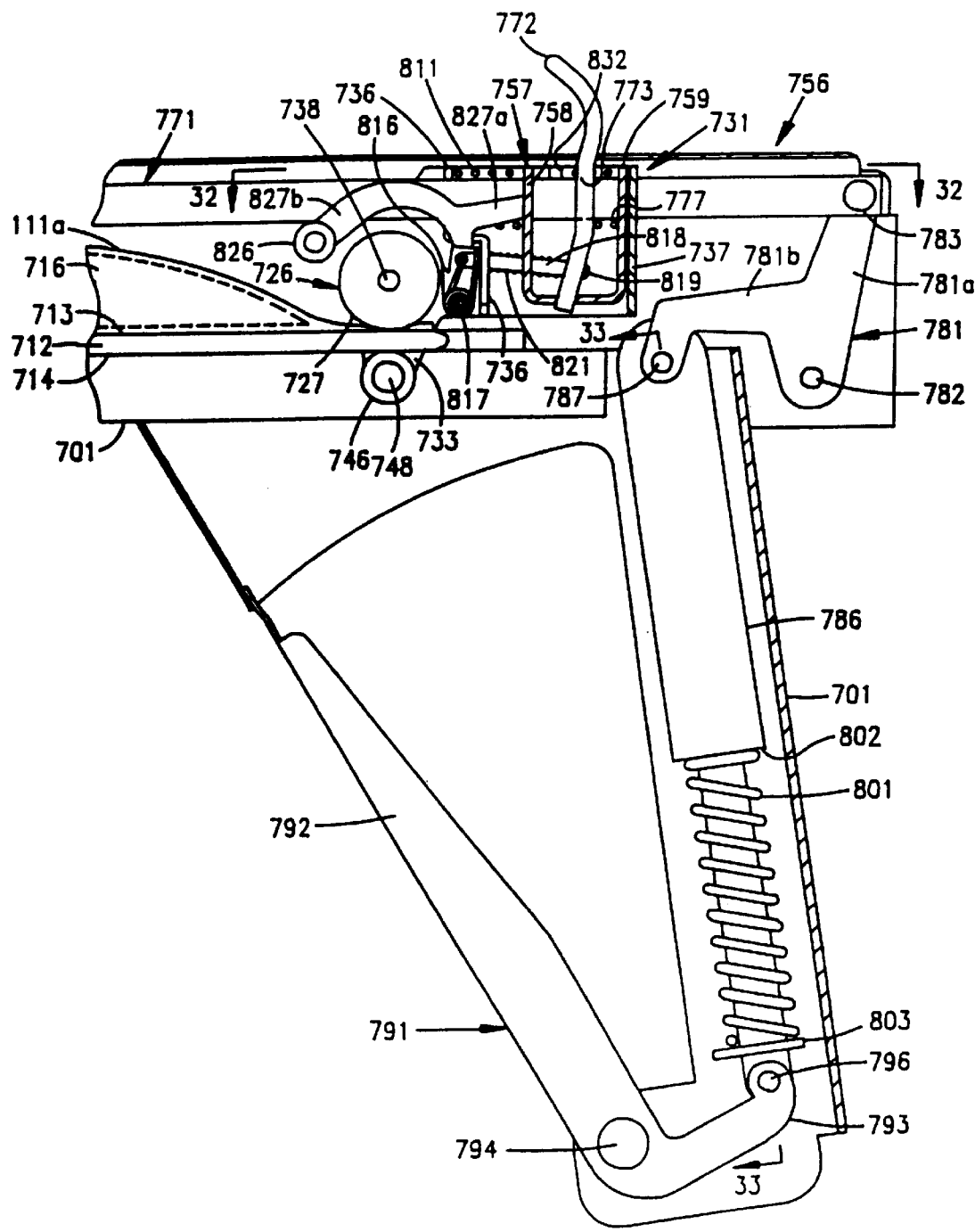
FIG. 30 is a fragmentary cross-sectional view of the delivery apparatus of FIG. 29 taken along the line 30—30 of FIG. 32.
Figure 31:
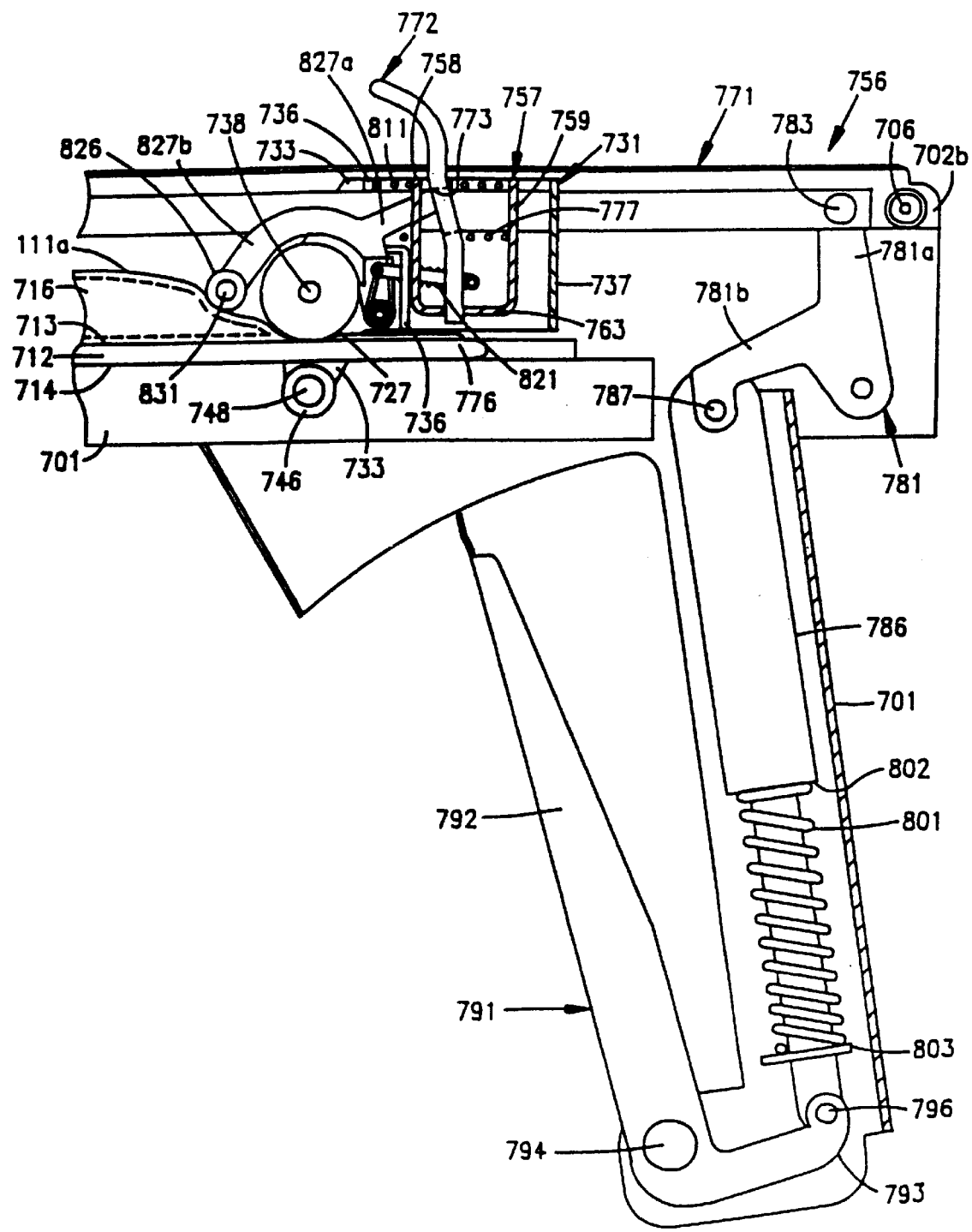
FIG. 31 is a fragmentary cross-sectional view similar to FIG. 30 of the delivery apparatus of FIG. 29.

Roller means in the form of cylindrical roller 726 is provided for longitudinal travel along upper surface 713 of platform 712 to squeeze cement composition 716 from delivery tube 111 (see FIGS. 30–32). Squeezing roller 726 is made from any suitable material such as silicone rubber having a durometer ranging from 50 to 70 Shore A. The roller 726 has an outer cylindrical surface 727 and a diameter of approximately one inch. Means for mounting roller 726 on platform 712 includes a support member or carriage chassis 731 made from stainless steel or any other suitable material. Carriage chassis 731 has first or left and second or right planar side plates 732 and 733 and middle and back plates 736 and 737 extending perpendicularly between the spaced-apart side plates 732 and 733. Carriage chassis 731 is carried by upper portion 702 of device 53 by a bracket (not shown). Roller 726 is disposed forward of middle plate 736 and is rotatably mounted to the carriage chassis 731 by a pin 738 extending transversely and perpendicularly between left and right side plates 732 and 733. Means for retaining roller surface 727 firmly on upper surface 713 as the roller travels along platform 712 are provided.

Drive means or assembly 756 serves to move roller 726 forwardly along platform surface 713. Assembly 756 includes a box-shaped member or pusher 757 having front and rear walls 758 and 759, left and right walls 761 and 762 and a bottom wall 763 (see FIGS. 30–32). The pusher has an open top. Pusher 757 is sized for disposition within carriage chassis 731 with front and rear walls 758 and 759 of the pusher 757 opposing respective middle and back plates 736 and 737 of the chassis 731. An elongate cylindrical rod or thrust rod 771 extends substantially the entire length of housing chamber 711 in a direction parallel to platform 712. Openings are provided in the upper portions of middle and back plates 736 and 337 of carriage chassis 731 and front and rear walls 758 and 759 of pusher 757 for permitting thrust rod 771 to slidably extend therethrough. A vertically disposed cinch element or cinch 772 is carried by rod 771 within pusher 757. Strip-like cinch 772 has a slight S-like conformation, as shown in FIGS. 30–31, and is provided with a bore 773 extending through the upper portion of its opposite faces for receiving rod 771. The bottom end of cinch 772 seats within an opening 776 provided in bottom wall 763 of pusher 757 so that the cinch is pivotable relative to the pusher between a rearward position shown in FIG. 30 and a forward position shown in FIG. 31. Pusher 757, thrust rod 771 and cinch 772 are each made from any suitable material such as stainless steel. A coil spring 777 is coaxially disposed about thrust rod 771 between cinch 772 and rear wall 759 of pusher 757 so as to bias the cinch to its forward position. The top end of cinch 772 extends through a slot 779 provided in the top of upper portion 702 for permitting finger actuation of the cinch by the user of delivery device 53.

Longitudinal reciprocation of thrust rod 771 within delivery device 53 results in forward travel of pusher 757 along platform 712. In this regard, the size and shape of cinch 772 and bore 773 therein preclude thrust rod 771 from sliding forwardly through the bore 773. As a result, in the forward stroke of thrust rod 771, cinch 772 locks about rod 771 so that the cinch moves forwardly relative to platform 712 in unison with the rod 771. Cinch 772 remains in its forward position under the force of coil spring 777 during the rearward stroke of thrust rod 771. The rod 771 is permitted to slide freely through cinch bore 773 in the rearward stroke of the rod 771.

Figure 33:
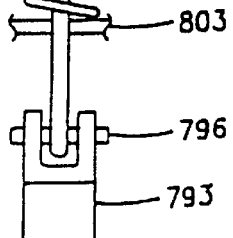
FIG. 33 is a fragmentary cross-sectional view of the delivery apparatus of FIG. 29 taken along the line 33—33 of FIG. 30.

Means for causing longitudinal reciprocation of thrust rod 771 is carried by handle 707 and includes a bell crank 781 pivotally mounted on housing 701 by a transversely extending pin 782 (see FIGS. 30–31 and 33). Bell crank 781 has a first arm 781a pivotally coupled to the rear end of thrust rod 771 by means of a fastener 783 and a second arm 781b pivotally coupled to an elongate element or puller 786 by means of a fastener 787. An L-shaped member 791 having a trigger 792 and an arm 793 extending at right angles to each other is pivotally carried by the bottom end of handle 707 by a transversely-extending pin 794. The bottom end of puller 786 is pivotally coupled to the free end of arm 793 by a fastener 796. Trigger 792 is thus pivotable about pin 794 between a first or home position shown in FIG. 30 and a second or actuated position shown in FIG. 31. Movement of the trigger 792 to its actuated position causes the rigid puller 786 to pivot first arm 781a of bell crank 781 forwardly. Thrust rod 781 moves forwardly in unison with the pivoting bell crank arm 781a. Trigger 792 is biased toward its home position by helical compression spring 801 mounted about the lower portion of puller 786. The first end of spring 801 abuts a shoulder 802 formed in puller 786 and the second end of spring 801 abuts a stop 803 rigidly attached to housing 701. Puller 786 slidably extends through stop 803. Thus, relaxation of the actuated trigger 792 causes thrust rod 771 to move back rearwardly to its home position shown in FIG. 30. Bell crank 781, puller 786 and L-shaped member 791 are each made from stainless steel or any other suitable material.

Pusher 757 is longitudinally movable in carriage chassis 731 between a rear or home position in which pusher rear wall 759 abuts chassis back plate 737, as shown in FIG. 30, and a forward or actuated position in which pusher front wall 758 abuts chassis middle plate 736, as shown in FIG. 31. Pusher 757 is biased toward its home position by a helical spring 811 concentrically mounted about thrust rod 771 and disposed in compression between chassis middle plate 736 and pusher front wall 758.

Pawl 816 is included within the means of delivery device 53 for restricting rearward rotation and movement of roller 726 on platform 712 while cinch 772 is in its forward position. Pawl 816 is pivotally mounted to carriage chassis 731 forward of middle plate 736 by a pin 817 extending perpendicularly between side plates 732 and 733 of the carriage chassis. An actuation element 818 is pivotally coupled at its front end to pawl 816. The rear end of the actuation element slidably extends through the opposite faces of cinch 772 and has a fastener 819 thereon abutting the cinch to preclude the actuation element from being pulled forwardly through the cinch. A coil spring 821 is mounted about actuation element 818 and abuts pawl 816 at its front end and cinch 772 at its rear.

An additional or anti-dribble roller 826 is provided for increasing the pressure on delivery tube 111 when squeezing roller 726 is moving forwardly along platform 712 and for decreasing the pressure on tube 111 when roller 726 is not moving forwardly along the platform 712. Compressive member or roller 826 has a diameter of approximately 0.25 inch and is made of the same material as squeezing roller 726. Roller 826 is mounted on carriage chassis 731 by means of first or left and second or right support arms 827 and 828 pivotally mounted in spaced apart positions on the ends of pin 817. The support arms have respective rear extensions 827*a* and 828*a* extending between respective pusher walls 761 or 762 and carriage side plates 732 and 733. A pin 833 protrudes inwardly from each of extensions 827*a* and 828*a* for slidable receipt within a vertical groove 832 extending downwardly from the top of the pusher side wall 761 or 762. Support arms 827 and 828 are each formed with respective forward extensions 827*b* and 828*b* which extend arcuately over squeezing roller 726. Roller 826 is rotatably mounted between the forward ends of extensions 827*b* and 828*b* by a pin 831. Forward movement of pusher 757 within carriage chassis 731 causes pins 833 to move upwardly within grooves 832 so as to pivot anti-dribble roller 826 from an out-of-the-way position shown in FIG. 30 to a lower operational position shown in FIG. 31.

Also provided by the subject invention are kits for use in applications where calcium phosphate cements are employed, where the subject kits at least comprise a storage means housing the two component cement according to the subject invention. The kits may further include the delivery device and/or the mixing device as described above. Also provide in the kits may be various tubular delivery means, such as needles, cannulas or other suitable delivery means for attaching to the sealing means and the exit port of the delivery device and introducing the material to the site of interest. The kits may further include instructions for preparing the cement housed in the storage means, where the instructions may be incorporated onto one or more of the labeling for the storage means, a package insert and/or the kit packaging.

The subject system described above finds use in applications where it is desired to introduce a flowable material capable of setting up into a solid calcium phosphate product into a physiological site of interest, such as in dental, craniomaxillofacial and orthopedic applications. In orthopedic applications, the cement will generally be prepared, as described above, and introduced to a bone repair site, such as a bone site comprising cancellous and/or cortical bone.

Orthopedic applications in which the cements prepared by the subject system find particular use include the treatment of fractures and/or implant augmentation, in mammalian hosts, particularly humans. In such fracture treatment methodologies, the fracture is first reduced. Following fracture reduction, a flowable structural material prepared by the subject system is introduced into the cancellous tissue in the fracture region using the delivery device described above. Specific orthopedic indications in which the subject invention finds use include: (1) the treatment of compromised vertebral bodies; (2) the treatment of vertebral body burst fractures; (3) pedicle screw augmentation; (4) the treatment of fractures of the distal radius; (5) the treatment of intertrochanteric hip fractures; (6) the treatment of femoral neck fractures; (7) the treatment of avascular necrosis; (8) the treatment of fractures of the tibial plateau; (9) the treatment of fractures of the calcaneus; (10) soft tissue reattachment; (11) the treatment of fractures of the proximal humerus; (12) vertebral fusions; (13) acetabular fractures; (14) pelvic fractures; (15) total joint arthroplasty, both primary and revision and the like. Each of these applications will be discussed in greater detail below.

I. The Treatment of Compromised Vertebral Bodies

Cements prepared with the subject system find use in the treatment of compromised vertebral bodies. By "compromised vertebral bodies" is meant vertebral bodies in which the cancellous bone mass is at least reduced as compared with vertebral bodies found in hosts which are not suffering from a bone remodeling disorder, i.e. normal controls. Typically, compromised vertebral bodies will be vertebral bodies which have been structurally altered, where such structural alteration will typically be in the form of compression or fracture, which compression and/or fracture may occur at one or more distinct regions of the vertebral body, but usually affects the anterior portion of the vertebral body. By treatment is meant that the progression of the structural alteration in the vertebral body is at least slowed, if not stopped. Treatment also includes situations where the compressive load capabilities and/or the original structure of the vertebral body are restored. Treatment also includes prophylactic treatment of vertebral bodies in which the cancellous bone mass is decreased as compared to that found in a normal control, but the vertebral body is not compressed or fractured. Of particular interest is the treatment of compression fractures with the subject methods.

In the subject methods, prior to introducing the calcium phosphate cement into the vertebral body, the compromised vertebral body may optionally be anatomically reduced, where methods of anatomical reduction of vertebral bodies are known by those of skill in the art. See Rockwood & Green (4th ed.) p 529 and references cited therein. Alternatively, in some situations it may be desirable to use the following approach to restore height to the compromised vertebral body. First, the structural material being employed, e.g. the calcium phosphate cement, may be introduced into the adjacent vertebral bodies and allowed to set. Following setting of the structural materials in the adjacent vertebral bodies, the compromised vertebral body may then be reduced. This procedure finds application in situations where the structural integrity of the adjacent vertebral bodies it not sufficient to withstand reductive forces.

Following preparation of the patient and any anatomical reduction of the fractured vertebral body, a suitable cement delivery/introduction means such as a large bore needle will be selected. Where large bore needles are employed, the gauge of the needle will generally range from about 6 to 16, usually from about 10 to 14 and more usually from about 12 to 14, where one of the main parameters considered in selection of the needle is the ability of the calcium phosphate cement to readily flow through the delivery means and the ability of the delivery means to fit within the site and patient specific pedicle.

Prior to introduction of the flowable calcium phosphate cement composition into the compromised vertebral body, the vertebral body may be flushed with warm saline or other suitable solution in order to remove any loose or dislodgeable matter present in the vertebral body, including fatty marrow matter and the like. Furthermore, the vertebral body may be flushed with cool saline or other suitable solution in order to reduce the temperature of the vertebral body which postpones the setting and may improve infiltration of the cement Where the vertebral body is so cooled, the temperature of the solution used to cool the vertebral body will generally be less than 25, usually less than 20, and generally greater than 0, usually around 4° C. In addition to the above site preparation steps, a venogram may be performed in order to assess vascular access.

In performing the above steps, as well as the cement introduction steps described below, the needle or other delivery means may be introduced into the vertebral body using a variety of methodologies as are known by those of skill in the art. Generally, the needle will be introduced using a posterolateral approach, preferably either perispinally or through the pedicle, usually through the pedicle.

The next step in the subject method is to fill at least a portion of, and up to and including substantially all of, the voids or spaces present in the cancellous bone region of the compromised vertebral body with the flowable calcium phosphate cement. Accordingly, depending on the nature of the compromised vertebral body being treated, e.g. decrease in bone mass and/or presence of compression fracture, as little as ⅓ of the vertebral body may be filled with the cement, where the portion of the vertebral body which is filled will generally be at least about ½ of the vertebral body. Sometimes substantially all of the vertebral body will be filled with the cement composition, whereby substantially all is meant at least 90%, usually at least 95%.

This step is generally accomplished by inserting the needle, as described above, so that the end of the needle is in the anterior region of the vertebral body. Where desired, pressure may then applied to move the calcium phosphate cement through the needle, where the pressure employed will not be excessive, and will generally just be sufficient to move the cement through the needle. As the cement begins to enter the vertebral body, the needle may be pulled out of the vertebral body to further infiltrate the adjacent cancellous bone with the cement, whereby the cancellous region of the vertebral body is further filled with the cement. The rate at which the needle is removed will generally be at least about 0.1 mm/s and usually at least about 1 mm/s but will generally not exceed about 10 mm/s. While the needle is being removed, cement will continue to be introduced through the tip of the needle. As the needle approaches complete exit, the delivery of cement through the needle should be stopped in order to minimize the back flow of cement out of the entry of the vertebral body and into the surrounding soft tissue.

Instead of, or in addition to, the application of pressure to the cement, cement delivery into and perfusation of the cement throughout the cancerous region of the compromised vertebral body being treated may be enhanced by applying external energy to the at least the region of cancellous bone where the presence of the calcium phosphate cement is desired. By external energy is meant physical energy, such as motion, which may be in the form of agitation, vibration, sonic wave and the like. Any means of introducing this external energy to the region of cancellous bone to be infiltrated may be employed. One convenient means of applying external energy to the region of the compromised vertebral body of interest is to vibrate the cement delivery means, where either the entire cement delivery means may be vibrated or just a portion of the delivery means may be vibrated, where preferably that portion of the delivery means proximal to the cancellous bone region of interest is vibrated, e.g. the delivery needle. Another means of introducing external energy to the desired site is to directly agitate the compromised vertebral body itself and/or the adjacent vertebral bodies. For example, to apply external energy directly to the compromised vertebral body, one may insert a second agitation device into the vertebral body. The amount of external energy which is introduced will not be excessive, but merely sufficient to promote efficient infiltration of the calcium phosphate cement composition throughout the cancellous bone region of interest.

To ensure that an adequate portion of the compromised vertebral body is filled with the cement composition, the progress of the filling of the vertebral body may be monitored using any convenient monitoring means, where such monitoring means include CT scanning, fluoroscopy, MRI, DEXA (dual energy x-ray absorptiometry) and the like, where such means are known to the those of skill in the art.

II. The Treatment of Vertebral Body Burst Fractures

Cements prepared with the subject system find use in the treatment of vertebral body burst fractures. To treat vertebral body burst fractures, the burst fracture is first decompressed and any bone protruding into the spinal canal is removed. Following decompression and removal of any protruding bone, a flowable calcium phosphate cement capable of setting in vivo into an apatitic product is introduced into any voids in the vertebral body resulting from decompression in an amount sufficient to substantially fill the voids. The introduced calcium phosphate cement is conveniently retained at the site of administration using a retaining means. The cement is then allowed to set, whereby the burst fracture is stabilized and treated. In treating vertebral body burst fractures, the subject methodology may be used in conjunction with spinal fusion methodologies.

III. Pedicle Screw Augmentation

The flowable materials produced by the subject systems are suitable for use in spinal fixation applications for pedicle screw augmentation. In such applications, the spine is first prepared for insertion of the pedicle screw according to known procedures and depending on the particle spinal fixation device to be employed. A variety of spinal fixation systems comprising pedicle screws are known in the art, including those described in U.S. Pat. Nos. 5,690,630; 5,634,925; 5,584,831; 5,545,163; 5,474,558; 5,366,455; 5,209,753; and 5,169,015; the disclosures of which are herein incorporated by reference. In preparing the spine, following exposure of the appropriate pedilce(s), a hole for the pedicle screw is then formed in the pedicle using a drill or other convenient means. Following drilling of the hole, the hole may be cleared of fluid and/or loose tissue or other matter, e.g. bone fragments and the like. An amount of flowable material prepared according to the subject invention sufficient to provide for stable placement of the pedicle screw in the hole is then introduced into the prepared hole with the delivery device of the subject invention, where the amount will generally range from about 0.5 to 5.0 ml, usually from about 0.5 to 3.0 ml, and more usually from about 1.0 to 2.0 ml. Following introduction of the flowable cement material and prior to setting of the flowable material, the pedicle screw is then inserted into the hole in its final position, where placement of the pedicle screw in final position usually is accomplished within 10 minutes of cement introduction, more usually within 5 minutes of cement introduction and preferably within 3 minutes of cement introduction. Following introduction of the pedicle screw and setting of the flowable material, the remainder of the spinal fixation application can be performed according to convention protocols.

IV. The Treatment of Fractures of the Distal Radius

The first step in treating a fracture of the distal radius according to the subject invention is the reduction of the fracture. Preferably, the fracture will be anatomically reduced such that restoration of the normal length, alignment and articular surface congruancy of the fractured distal radius is restored. Fracture reduction techniques suitable for use in the subject invention are well known in the art, see Rockwood & Greens's Fractures in Adults (1991) pp 592–599 (the disclosure of which is herein incorporated by reference) and include both open, e.g. via longitudinal dorsal, volar, limited transverse dorsal approaches, and closed reduction techniques, e.g. finger trap traction, and the like. Depending on the nature of the fracture, as well as the manner in which it is reduced, fracture reduction may result in the formation of a void or open space in the cancellous bone of the fracture region, where such a void is the result of compression of the cancellous bone during fracture without decompression of such bone upon fracture reduction.

The next step in the subject methods is the preparation of a cancellous bone fracture void. Cancellous bone fracture void preparation comprises at least producing a fracture void in the cancellous bone of the distal radius in the region of the fracture, where the void will usually traverse (i.e. span, bridge, cross-over) the fracture line so as to be produced in portions of the cancelous bone on both sides of the fracture line.

In those instances where the reduction of the fracture results in bone void, the cancelous bone fracture void is prepared by at least expanding the volume of the void which is already present as a result of the fracture reduction. By at least expanding the already present void is meant that the void volume is increased by at least about 300%, usually by at least about 500% and more usually by at least about 1000% from its initial volume following fracture reduction, where the void may be expanded all the way to outer cortices of the distal radius, proximally, medially and laterally. The void volume may be expanded using any convenient means capable of compressing the cancellous bone in the void. For example, one could employ a rongeur awl, and the like.

Preparation of the cancellous bone fracture void also comprises those embodiments of the subject invention where the cancellous bone is removed and/or compressed in the region of the distal radius in a manner sufficient to produce a cancellous bone void which has a fracture stabilizing shape, where the term fracture stabilizing refers to a shape that serves to provide internal stabilization to the fracture and includes cementing, filling the void, and the like, where shapes approximating the inner surface of the cortical bone of the distal radius in the region of the fracture are preferred.

During preparation of the cancerous void volume, the void may be cleared of any tissue, fluid or other material one or more times during the preparation, as needed, using any convenient means, such as suction, Frazier tip, forceps and the like, where such clearing may further comprise the introduction of a biologically compatible solution which assists in the clearing, such as a saline solution, water, ringers solution and the like, where the solution may be cooled in order to reduce the temperature of the void. When cooled solutions are employed, the temperature of such solutions will typically range from about 5 to 37° C., usually from about 5 to 20° C. and more usually from about 15 to 20° C.

Following preparation of the cancellous bone void fracture volume, a structural material as described above, e.g. a flowable calcium phosphate cement capable of setting in vivo into a solid apatite product such as carbonated apatite, is introduced into the prepared cancellous bone fracture void. The structural material may be introduced using any convenient delivery means. The particular delivery means employed will necessarily depend on the nature of the structural material to be introduced into the prepared void. Since the structural material will typically have a flowable paste like consistency, usually a syringe, cannula or other such delivery means will be employed. For use with the preferred flowable calcium phosphate cements, typically the delivery means that is employed will be a needle having a gauge of sufficient size to allow passage of the flowable material. Usually a needle having a gauge ranging from about 8 to 16, usually from about 9 to 16 and more usually from about 12 to 14 will be employed as the delivery means.

The amount of structural material that is introduced into the prepared void will be sufficient to substantially fill the entire void volume, where by substantially fill is meant that the amount introduced will be sufficient to fill at least about 95%, usually at least about 98% and more usually at least about 99% of the void volume and infiltration to adjacent cancellous bone.

Following introduction of the structural material into the prepared void, the structural material will then be allowed to set into a solid product that substantially fills the void volume, where the term substantially fills means the same as defined above.

Depending on the nature of the structural material, the treatment of the fracture may further comprise immobilization of the distal radius at least in the region of fracture for a time sufficient for the structural material to fully harden or cure into a solid product. For example, with the calcium phosphate structural materials of the preferred embodiment of the subject invention, the distal radius in at least the region of the fracture will be immobilized for a period of less than about 8 weeks, usually less than about 6 weeks and more usually less than about 4 weeks, where the period of time may be less than 2 weeks and even less than 1 week. Any convenient means of immobilization may be employed, where such means include use of casts, where the casts may be fabricated from a variety of different materials, including plaster, polymeric materials, moldable metals and the like, where the preparation and use of casts is well known to those of skill in the art.

The subject invention may be used in combination with fixation devices, where such devices may be external fixation devices, such as percutaneous fixation devices, e.g. K wires, pins and the like, or internal fixations devices, e.g. bone screws and plates. When used in combination with fixation devices, the fixation devices will preferably not be inserted into or through the structural material, particularly through such materials whose final set properties, such as strength, integrity and the like, might be compromised from removal of the fixation device, e.g. calcium phosphate cements. These devices will be left at the fracture site until sufficient healing occurs to fully stabilize the anatomical site.

V. The Treatment of Intertrochanteric Hip Fractures

The flowable materials produced with the subject system find use in the treatment of intertrochanteric hip fractures. In such applications, the flowable cement material is used in conjunction with a sliding hip screw device which comprises at least a lag screw and a side plate components. A variety of sliding hip screw devices are known to those of skill in the art and include those described in U.S. Pat. Nos. 5,562,666; 5,492,442; 5,312,406; 5,167,663; 5,032,125; and 4,657,001, the disclosures of which are herein incorporated by reference.

In treating introchanteric hip fractures according to the subject invention, the first step is to reduce the fracture. Methods for reducing intertrochanteric hip fractures are known to those of skill in the art and described in Rockwood & Greens's Fractures in Adults (1996), the disclosure of which is herein incorporated by reference.

Following fracture reduction, the lag screw component of the particular sliding hip screw device to be employed is introduced into position. To introduce the lag screw, generally a lag screw guide wire will first be inserted into position with the aid of imaging means, e.g. fluoroscopic imaging means. Following introduction of the guide wire, the lag screw hole will be prepared by triple reaming, as is known in the art. Following triple reaming, the lag screw is introduced into position.

Following lag screw placement, a void is prepared in the cancellous bone in the region of the fracture. By void preparation is meant that a region of the cancellous bone is cleared of both bony and soft tissue and other materials to provide an open space which is at least partially surrounded by areas of compressed cancellous bone. The voids are prepared using a curette or other suitable device to compress and/or remove weak cancellous bone in the void region. All blood clots, bone debris and the like are removed from the void site using irrigation or other suitable means. Following void preparation, the void area(s) is assessed to provide for adequate fill in the cement introduction step, as described in greater detail below.

The next step of the subject method is critical and comprises a trial placement of the side plate component of the sliding hip screw device in order to ensure that the side plate will be easily and correctly positioned following introduction of the cement material. After the side plate has been inserted and evaluated for proper positioning, it is then removed.

Next, the flowable material is introduced into the prepared voids. The cement is usually introduced by moving the delivery needle or similar means in a retrograde fashion. Preferably, the supero-lateral void is filled first, followed by filling of the supero-medial void, and inferior voids. Preferably, each of the voids, and in particular the inferior voids, are maximally filled. To ensure sufficient filling of the void spaces, filling is preferably performed under image enhancement. The cement introduction period will be relatively rapid, usually not exceeding 8 minutes, more usually not exceeding 6 minutes and preferably not exceeding about 5 minutes.

Following cement introduction, the slide plate is placed into final position. Critical to the subject invention is positioning of the side plate prior to setting of the cement, usually within 5 minutes, more usually within 3 minutes and preferably within 2 minutes of cement introduction.

Following insertion of the side plate, the cortical screw(s) of the side plate will be inserted thereby further fixing the side plate in position. Optionally, additional cement material may be introduced through a cortical screw hole of the side plate, e.g. the first cortical screw hole, prior to introduction of the cortical screw and order to further enhance fixation.

The fracture is then maintained in a stable position, i.e. it is not manipulated, for a period of time sufficient for the flowable material to set into a hardened product, usually for a period of at least about 10 minutes.

The subject methods of treating intertrochanteric hip fractures provide a number of advantages, including stable reduction, the development of a structural medial buttress, complete filling of the distal portion of the device with a structural material, and the like, which provide for improved patient results.

VI. The Treatment of Femoral Neck Fractures

The cements prepared according to the subject system find use in the treatment of fractures of the femoral neck. In treating fractures of the femoral neck with flowable cement materials produced according to the subject system, the first step is to reduce the fracture. Methods of reducing femoral neck fractures are well known in the art. See Rockwood & Greens's Fractures in Adults (1996) (the disclosure of which is herein incorporated by reference). Following fracture reduction, holes for the femoral neck fixation means are prepared, where the type of hole prepared will necessarily depend on the nature of the fixation means to be used. Fixation means finding use in the subject methods include screw type devices as disclosed in U.S. Pat. Nos. 5,573,436; 5,431,651; 5,167,663; RE 33,348; and the like, as well as non-screw type fixation devices, such as those described in U.S. patent application Ser. No. 60/046,668 entitled Rebar Bone Fixation Devices, the disclosures of which are herein incorporated by reference. In the subject methods, at least one fixation means, usually at least two fixation means, and not more than about 5 fixations means, and usually not more than about 3 fixations means will be employed. Associated with the introduction of at least one of the fixation means into the prepared holes is the introduction of a flowable material prepared with the subject system into the hole, where introduction typically occurs prior to insertion of the particular fixation means. The amount of flowable material introduced into the hole generally ranges from about 0.2 o 2.0 cc, and usually from about 0.5 to 1.0 cc. The fixation means will be introduced into the hole comprising the flowable material prior to setting of the flowable material, typically within 10 minutes, usually within 5 minutes and more usually within 2 minutes of cement introduction. The region of the fracture is then maintained in a stable position for a sufficient period of time for the cement to harden, usually a period of time of at least about 10 minutes. Additional cement may then be introduced into the fracture void. By using the above protocol, the femoral neck fracture is treated, whereby treated is meant femur is stably positioned relative to the trochanteric region of the hip.

VII. The Treatment of Avascular Necrosis

Cements prepared according to the subject system find use in the treatment of a host suffering from avascular necrosis. In the subject methods, the osteonecrotic region(s) is first prepared by removing at least a portion of the necrotic tissue from the region to produce a prepared bone void, where the void may optionally be prepared to provide for optimal structural load characteristics. Next, a flowable structural material capable of setting in vivo into a solid product is introduced into the prepared void and allowed to harden. The subject methods find use in the treatment of a variety of osteonecrotic conditions, and are particularly suited for use in the treatment of femoral head avascular necrosis. Critical to the subject methods is the preparation of a bone void in the region of osteonecrotic bone. In preparing the bone void, at least a portion of the nectrotic bone tissue in the osteonectrotic region will be removed. Any convenient device for preparing the bone void through removal of the necrotic tissue may be employed, where suitable devices are known in the art.

In a preferred embodiment, the prepared bone void is produced in such a manner so that the hardened structural material introduced thereto is self-retraining and distributes load towards the cortical bone at the periphery of the femoral head. As such, a preferred bone void will have a reverse-taper cut such as, e.g. a reverse conical shape, where the cross-section area of the void decreases as one moves towards the bone void entrance at the cortical surface.

The particular approach used to prepare the bone void will necessarily depend on the specific nature of the bone in which the avascular or osteonecrotic region is present. Where the subject methods are used in the treatment of femoral head avascular necrosis, one preferred method of preparing the cancellous bone void involves the use of a "trap-door" approach.

In preparing the bone void, the void may be cleared of any tissue, fluid or other material one or more times during the preparation, as needed, using any convenient means, such as suction, lavage, forceps, curette and the like, where such clearing may further comprise the introduction of a biologically compatible solution which assists in the clearing, such as a saline solution, water, ringers solution and the like, where the solution may be cooled in order to reduce the temperature of the void. When cooled solutions are employed, the temperature of such solutions will typically range from about 5 to 37, usually from about 5 to 20 and more usually from about 15 to 20° C.

In those embodiments where the avascular necrosis is due to a traumatic event such as a femoral neck fracture and the like, the fracture may be reduced prior to preparation of the bone void. Methods of fracture reduction suitable for a particular indication and known to those of skill in the art may be employed.

Following preparation of the bone void, a structural material as described above, e.g. a flowable calcium phosphate cement capable of setting in vivo into a solid apatite product such as carbonated apatite, is introduced into the prepared bone void. The structural material may be introduced using any convenient delivery means. The particular delivery means employed will necessarily depend on the nature of the structural material to be introduced into the prepared void. Since the structural material will typically have a flowable paste like consistency, usually a syringe, cannula or other such delivery means will be employed. For use with the preferred flowable calcium phosphate cements, typically the delivery means that is employed will be a needle having a gauge of sufficient size to allow passage of the flowable material. Usually a needle having a gauge ranging from about 8 to 16, usually from about 9 to 16 and more usually from about 12 to 14 will be employed as the delivery means.

The amount of structural material that is introduced into the prepared void will be sufficient to substantially fill the entire void volume, where by substantially fill is meant that the amount introduced will be sufficient to fill at least about 95%, usually at least about 98% and more usually at least about 99% of the void volume and infiltration to adjacent cancellous bone.

Following introduction of the structural material into the prepared void, the structural material will then be allowed to set into a solid product that substantially fills the void volume, where the term substantially fills means the same as defined above.

While the treated region may be kept immobile for an extended period of time following introduction of the structural material, generally the host will be allowed to move the region following the initial set of the structural material. If the region is immobilized for an extended period of time, such a period of time will usually not exceed about 24 hours and more usually will not exceed about 72 hours. By treated is meant that the a substantial portion of the necrotic tissue of the patient is replaced with the structural material. Treated also encompasses those situations where the patient achieves an earlier return to function.

VIII. The Treatment of Fractures of the Tibial Plateau

Turning now to the subject methods, the first step in treating a fracture of the distal radius according to the subject invention is the reduction of the fracture. Fractures suitable for treatment according to the subject methods may be depressed split-depressed or complex. Preferably, the fracture will be substantially anatomically reduced. Fracture reduction techniques suitable for use in the subject invention are well known in the art. See Rockwood & Greens's Fractures in Adults (1996) pp 1919–1954 (the disclosure of which is herein incorporated by reference).

Fracture reduction with tibial plateau fractures will result in the production of one or more cancellous bone defects or voids, depending on the complexity of the fracture. In other words, fracture reduction results in the production of one or more initial cancellous bone voids. The initial cancellous bone voids will typically range in volume from about 1 to 20, and will usually range in volume from about 5 to 15 cm$^3$.

The next step in the subject methods is the production of the prepared cancellous bone fracture void(s). Cancellous bone fracture void preparation comprises at least producing a fracture void in the cancellous bone of the tibia in the region of the fracture, where the void traverses the fracture line so as to be produced in portions of the cancelous bone on both sides of the fracture line.

In those instances where the reduction of the fracture results in an initial bone void, such as the reduction of a depressed fracture, the cancelous bone fracture void is prepared by at least expanding the volume of the void which is already present as a result of the fracture reduction. By at least expanding the already present or initial void is meant that the void volume is increased by at least about 300%, usually by at least about 250% and more usually by at least about 200% from its initial volume following fracture reduction.

In one embodiment of the subject invention, the prepared fracture void will have an inverse shape. By inverse shape is meant that the prepared fracture void will have a base cross-sectional area that is greater than its surface cross-section area, where the surface cross-sectional area is the area of the void substantially proximal to the plateau surface of the tibia and the base is distal thereto. The inverse shaped prepared bone void can be further characterized by a variety of different shapes, such as conical, pyramidal, irregular and the like.

In another embodiment of the subject invention, the prepared void substantially has a shape that is congruous with the internal cancellous region of the tibial plateau, i.e. corresponds to the region bounded by the cortical bone.

The prepared cancellous bone void may be prepared using any convenient means, such as awl, bone tamp, and the like.

During preparation of the cancelous void volume, the void may be cleared of any tissue, fluid or other material one or more times during the preparation, as needed, using any convenient means, such as irrigation with saline and suction, and the like, where such clearing may further comprise the introduction of a biologically compatible solution which assists in the clearing, such as a saline solution, ringers solution, and the like, where the solution may be cooled in order to reduce the temperature of the void. When cooled solutions are employed, the temperature of such solutions will typically range from about 5 to 25, usually from about 10 to 20 and more usually from about 15 to 20° C.

Following preparation of the cancellous bone void fracture volume, a structural material as described above, e.g. a flowable calcium phosphate cement capable of setting in vivo into a solid apatite product such as carbonated apatite, is introduced into the prepared cancelous bone fracture void. The structural material may be introduced using any convenient delivery means. The particular delivery means employed will necessarily depend on the nature of the structural material to be introduced into the prepared void. Since the structural material will typically have a flowable paste like consistency, usually a syringe, cannula or other such delivery means will be employed. For use with the preferred flowable calcium phosphate cements, typically the delivery means that is employed will be a needle having a gauge of sufficient size to allow passage of the flowable material. Usually a needle having a gauge ranging from about 9 to 16, usually from about 10 to 14 and more usually from about 10 to 12 will be employed as the delivery means.

The amount of structural material that is introduced into the prepared void will be sufficient to substantially fill the entire void volume, where by substantially fill is meant that the amount introduced will be sufficient to fill at least about 95%, usually at least about 98% and more usually at least about 99% of the void volume.

Following introduction of the structural material into the prepared void, the structural material will then be allowed to set into a solid product that substantially fills the void volume, where the term substantially fills means the same as defined above.

Depending on the nature of the structural material, the treatment of the fracture may further comprise maintaining the treated tibia at least in the region of fracture for in a non-weight bearing state for a time sufficient for the structural material to fully harden or cure into a solid product. For example, with the calcium phosphate structural materials of the preferred embodiment of the subject invention, the tibia in at least the region of the fracture will be immobilized for a period of at least about 1 week, usually at least about 4 weeks and more usually at least about 6 weeks, where the non-weight bearing state will be maintained for a period that typically does not exceed 12 weeks and usually will not exceed 8 weeks. Any convenient means of maintaining a non-weight bearing state may be employed, such as crutches, walkers, and the like.

The subject invention may be used in combination with fixation devices, where such devices may be external fixation devices, percutaneous fixation devices, e.g. K wires, pins and the like, or internal fixations devices, e.g. bone screws and plates. Of particular interest in many embodiments of the subject invention is the use of the subject methods in conjunction with internal fixation hardware, such as bone screws and plates. A variety of bone screw and plate devices suitable for use in the treatment of tibial fractures are known to those of skill in the art, including those described in U.S. Pat. No. 4,936,884, the disclosure of which are herein incorporated by reference.

The subject methods result in the treatment (i.e. recovery) of tibial plateau fractures, where by treatment is meant that the patient at least regains partial use, if not complete use of the tibia and/or the pain of the fracture is at least reduced, as compared to a control. Preferably, the subject methods result in full recovery of the use of the tibia.

IX. The Treatment of Fractures of the Calcaneus

In treating calcaneal fractures according to the subject invention, typically the first step is reducing the calcaneal fracture. Methods of reducing calcaneal fractures are known to those of skill in the art and are reviewed in Rockwood & Green's Fractures in Adults, supra. The particular method of fracture reduction will vary depending on the nature of the fracture being treated, but will generally be performed with the goal of restoring anatomical configuration to the calcaneus, where restoration of articular continuity of the subtalar joint is of particular interest. Reduction of the fracture will generally result in the formation of a cancellous bone void.

Following fracture reduction, a flowable structural material, as described above, will be introduced into at least a portion of the cancellous region of the reduced fracture in an amount sufficient to substantially fill the void spaces present in portion of the cancellous region. Thus, the structural material may be introduced into the cancellous region in a manner sufficient to substantially fill all of the void spaces present in the cancellous region due to reduction of the fracture and any void preparation, where the term "void spaces," as used herein does not include spaces of the inherently porous nature of the cancellous bone, though such porous spaces could be filled, at least partially, in the course of the subject methods. Alternatively, the material may be introduced in a manner such that substantially all of the void spaces are filled in only a portion of the calcaneal cancellous bone. In any event, by "substantially all" is meant that at least 90%, usually at least 95% and more usually at least 99% of the void space is filled in the region of interest.

The structural material may be introduced into the cancellous region of the calcaneus using an convenient methodology, where usually the methodology employed will include the use of a large bore needle, where the gauge of the needle will generally range from about 6 to 16, usually from about 10 to 14 and more usually from about 10 to 12, where one of the main parameters considered in selection of the needle is the ability of the calcium phosphate cement to readily flow through the delivery needle and the ability of the surgeon to access the void.

Prior to introduction of the structural material into the calcaneus, the calcaneal cancellous region may be flushed with warm saline or other suitable solution in order to remove any loose or dislodgeable matter present in the region, including fatty marrow matter and the like. Furthermore, the cancerous region may be flushed with cool saline or other suitable solution in order to reduce the temperature of the calcaneus which postpones the setting and may improve infiltration of the cement. Where the calcaneus is so cooled, the temperature of the solution used to cool the calcaneus will generally be less than 25, usually less than 20, and generally greater than 0, usually around 4° C.

Optionally, the cancellous bone void may be prepared prior to introduction of the structural material, where by prepared is meant that the cancellous bone immediately adjacent to the void is at least partially compressed or removed in a manner sufficient to enlarge the void volume.

The next step in the subject method is to fill at least a portion of, and up to and including substantially all of, the voids or spaces present in the cancellous bone region of the calcaneus. This step is generally accomplished by inserting the needle into the region to be filled. Where desired, pressure may then applied to move the calcium phosphate cement through the needle or analogous introduction means, where the pressure employed will not be excessive, and will generally just be sufficient to move the cement through the needle. As the cement begins to enter the cancellous bone, the needle may be pulled out of the calcaneus to further infiltrate the adjacent cancellous bone with the cement, whereby the cancellous region of the calcaneus is further filled with the cement. The needle will be withdrawn at a rate that will allow some pressurization of the cement in the cancellous bone void to permit maximal filling of the void and infiltration into adjacent cancellous bone at the periphery of the void. The rate at which the needle is removed will generally be at least about 0.1 mm/s and usually at least about 1 mm/s but will generally not exceed about 10 mm/s. While the needle is being removed, cement will continue to be introduced through the tip of the needle. As the needle approaches complete exit, the delivery of cement through the needle will usually be stopped in order to minimize the back flow of cement out of the entry of the calcaneus and into the surrounding soft tissue.

Following introduction of the structural material into the calcaneus, the structural material will be allowed to set into the solid product. In allowing the material to set, the calcaneus will be maintained in an immobile state for a sufficient period of time for the material to set.

The subject methods may be used in conjunction with a fixation means to maintain fracture reduction and/or calcaneal immobilization during at the least the period in which the cement is setting. Any fixation means of maintaining the calcaneus in an immobile state may be employed, where such means include: external means, such as casts; percutaneous means, such as K-wires; internal fixation means, such as plates and bone screws; and the like. Depending on the nature of the fracture being treated, the fixation means may be intended to be present on a temporary or permanent basis. For example, K-wires may be employed to maintain fracture reduction prior to and during cement introduction and setting. Following setting of the material into a solid product, the K-wires may then be removed.

Additional fixation means, when employed, may be introduced prior to or after introduction of the flowable structural material. The time at which the fixation means is introduced necessarily depends on the specific type of additional fixation means being employed. For example, where the fixation means is a cast, the fixation means will be employed after the structural cement material has been introduced into the void. Conversely, where internal hardware fixation means are employed, the cement will generally be introduced after implantation of the fixation means.

In this manner, calcaneal fractures are treated. By treated is meant that there is at least an improvement in the condition of the host being treated, where by at least improvement is meant that at least one of pain or gait problems associated with the fracture are reduced or alleviated as compared to the situation where no treatment was made. In many instances the subject methods result in a substantially complete elimination of pain and a return to full range of motion.

X. Soft Tissue Attachment

In using the cements prepared by the subject system for soft tissue anchorage, the structural material is used to stably attach the soft tissue to the surface of the bone. In a first embodiment of the subject invention, a cancelous bone void is prepared at the site of desired soft tissue attachment, a portion of the soft tissue, e.g. the end of a tendon or ligament, is introduced into the bone void in combination with a volume of the flowable structural material sufficient to substantially fill any void spaces in the void, and the structural material is allowed to set into a solid product, whereby the soft tissue becomes stably attached to or associated with the bone surface. In this embodiment of the subject invention, which may be recognized by those of skill in the art as a "potting" procedure, any convenient void shape may be employed. For "potting" the soft tissue in the void, the flowable structural material may be introduced first followed by introduction of the tissue, or vice versa, or the two may be introduced at substantially the same time, with the order of introduction being chosen as a matter of convenience based on the particular procedure being performed.

The bone voids employed in the subject invention may be standard shaped, tapered or inverse tapered. By standard is meant that the bone void comprises a substantially planar bottom surface bound or encircled by substantially perpendicular walls, such as found in cylindrical shaped voids. By tapered is meant that the cross-sectional area of the bone void gradually decreases as the one moves into the cancellous bone from the cortical bone surface, such as found in cone shaped voids. By inverse tapered is meant that the bone void is shaped such that compression forces are placed on the structural material when outward tension is placed on the soft tissue associated therewith, where by "outward tension" is meant tension directed away from the bone surface. Inverse shaped bone voids are characterized by having a base plane with a cross-sectional area that is larger than the top plane, usually by a factor of at least about 1.1, more usually by a factor of at least about 1.5, where the base plane is located in the bottom region of the void shape distal from the bone surface and the top plane is located at substantially the surface of the bone at the desired site of soft tissue attachment. Depending on the means employed to prepare the inverse shaped void, the void could be pyramidal shaped, conical shaped, irregular shaped, and the like, and have a "dove-tail" cross sectional shape. Generally, the inverse shaped bone void will be conical in shape, having a larger circular base than the top portion of the void. The volume of the inverse shaped bone void may vary widely depending on the particular nature of the soft tissue anchorage to be accomplished, with parameters affecting volume including the particular bone and soft tissue, the nature of the anchoring means and the like. Overall the size of the bone voids prepared in the subject methods will range from 0.1 to 5.0 cc, usually from about 0.1 to 4.0 cc. For larger voids, e.g. for use with bone plugs in ACL reconstruction, as described in greater detail below, the void volume will usually range in size from about 1.0 to 5.0 cc, more usually from about 1.0 to 4.0 cc. For smaller inverse shaped voids, e.g. for use with anchors, the volume will generally range from about 0.1 to 1.0 cc, usually from about 0.2 to 0.8 cc and more usually from about 0.2 to 0.4 cc.

To prepare the inverse shaped void, a variety of different means may be employed. The void may be prepared using standard probes, spatulas and the like in a purely manual fashion whereby the spongy cancellous bone region of the bone in which the void is to be prepared is compressed to produce the void. Alternatively, drilling means may be employed. Drilling means that may be employed include conventional drilling means which result in a standard cylindrical shaped bone void, where the drilling means may be cannulated for use with a guide wire, as is known in the art. For preparation of the inverse shaped bone void, a graduated drilling means may be employed which results in the preparation of a conical shaped bone void. Depending on the nature of the bone to which the soft tissue is to be attached, a drilling means that expands in width as it travels into the bone may be employed to prepare the inverse shaped bone void. Such drills may include a bit or similar device that can deploy a vane or cutting edge to create the undercut "dove-tail" beneath the cortex of the bone. Alternatively, a hand device that expands and can be used as a rasp to shape the void may be employed.

In certain embodiments of the subject methods, a soft tissue anchoring means is used to stably associate the soft tissue with the hardened structural material. In such methods, following preparation of the bone void, the soft tissue anchoring means is introduced into a the bone void followed by introduction of the flowable structural material.

The soft-tissue anchoring means may be either pre-attached to the soft tissue, or comprise a securing means, such as a suture etc., which suture may or may not be combined with a bone securing component, such as a base, for attaching the soft tissue to the bone. Examples of anchoring means that comprise the soft tissue pre-attached include bone-soft tissue grafts, where the grafts may be autologous, syngeneic, allogeneic or xenogeneic, and will preferably be autologous. Such anchoring means include patellar tendon grafts, hamstring tendon grafts, central quadriceps grafts and the like.

Alternatively, synthetic bone anchoring devices comprising means for lashing the soft tissue to the bone anchored device, such as a suture or the like, may be employed. The synthetic bone anchoring means may consist solely of a surface, where the suture may be simply looped in the bone void and stably secured therein by the flowable structural material as described in greater detail below, or may be knotted, where preferably the suture is simply looped in the void. The synthetic bone anchoring means may be more complicated, further comprising a bone securing means or other components, such as a base and the like, which may be configured to secure into the bone, such as by having ridges, barbs or other grasping means on its surface. A variety of different bone anchoring devices with different methodologies of use have been developed and are suitable for use in the subject methods. Such devices include those described in U.S. Pat. Nos.: 5,643,320; 5,634,926; 5,601,558; 5,584,385; 5,522,843; 5,501,696; 5,501,683; 5,500,001; 5,472,452; 5,441,502; 5,411,522; 5,380,334; 5,372,604; 5,370,662; 5,013,316; 4,744,353; the disclosures of which are herein incorporated by reference.

Where anchoring means are employed, following introduction of the anchoring means into the bone void, the flowable structural material will be introduced into the bone void and allowed to harden, whereby the anchoring means will become embedded in the void. As in those embodiments that do not employ an anchoring means, the amount of structural material that is introduced into the bone void will be sufficient to substantially fill any unoccupied spaces in the bone void.

In those embodiments where the soft tissue is pre-attached to the anchoring means, as described above, following hardening of the structural material the soft tissue will be stably associated with the bone surface.

Alternatively, where a synthetic anchoring means is employed in which the soft tissue is not pre-attached, the method will further comprise attaching the soft tissue to the synthetic anchoring device. The procedure for securing the soft tissue to the anchoring device will necessarily vary depending on the particular nature of the anchoring device employed. Generally, with those devices comprising a suturing means, the soft tissue will be lashed to the anchoring device by means of the suture using techniques known to those of skill in the art.

Where the anchoring means consists solely of a suture, a suture introduction device may be employed. Suture introduction devices that find use in the subject invention comprise an elongate member and a movable suture positioning means associated therewith. The elongate member will be sufficiently long for placing the suture loop into the bottom of the prepared void, where the length will generally range from about 2 to 15 cm, usually from about 5 to 10 cm. The elongate member may be solid or hollow, e.g. cannulated, such as needle, and may be made of any convenient material, such as stainless steel, plastic and the like, where a hollow elongate member, such as a needle, is preferred, since such an elongate member can also be used to introduce the flowable structural material into the void. The movable suture placement means will be capable of stably securing the suture to the elongate member during introduction of the elongate member into the void and then will be capable of maintaining the suture in position in the void while the elongate member is withdrawn. The suture introduction device may further comprise a notch at the distal end for further securing the suture to the elongate member during introduction. In some embodiments, it may be desired to have a suture that is capable of being pulled. In such embodiments, the suture will be introduced in conjunction with a "u" shaped tube fabricated from a suitable material, such as the same material as the suture, where the tube provides a tunnel in the hardened cement for movement of the suture.

By way of further illustration, the use of the subject invention using a physiological anchoring means, such as an autologous bone-tendon graft, will be discussed in greater detail in terms of the use of the subject methods in ACL reconstruction. One way of performing ACL reconstruction applications in which the subject methods are employed is as follows. First, bone tunnels will be prepared through both the femur and the tibia according to methods known in the art. A suitable graft will be harvested, where the graft will usually be a bone-tissue-bone graft, such as the patellar tendon grafts, central quadriceps grafts and the like, as described above. In this embodiment, the bone plug which is destined to reside in the femur will be cut in a tapered fashion, and the femoral tunnel will also be cut in a tapered fashion to produce an inverse shaped bone void, as described above, for the plug. Following introduction of the graft into position, the structural material will be introduced into the femoral bone tunnel behind and around the bone plug and allowed to harden, thereby securing the bone plug into position. Next tension will be applied to the soft tissue from the tibial side, and the tibial bone plug may be attached and secured using standard interference screws, as is known in the art. Alternatively, the flowable structural material could be employed to secure the tibial bone graft.

The subject methods find use in any application in which soft tissue anchorage to bone is desired, where soft tissue types that may be anchored to bone using the subject methods include tendons, ligaments, capsules and the like; where applications in the subject methods find use include: ACL reconstruction, PCL (posterial cruciate ligament) reconstruction, treatment of shoulder rotator cuff injuries, treatment of elbow and ankle injuries involving dissociation of soft tissue from bone, anterior gleno-humeral dislocations of the shoulder, and the like. The subject methods also find use in those applications where it is desired to attach one bone to another.

Kits for use in practicing the subject methods are also provided. Generally, the kits will comprise the components for preparation of the flowable structural material, such as the dry and liquid components of the calcium phosphate cements describe above. The kits may further comprise instrumentation, such as the novel expandable drilling means, and the like for use in preparing the inverse shaped bone voids. Finally, the kits may further comprise instructions for performing the subject methods in a variety of different applications, such as ACL reconstruction, soft tissue anchorage with or without bone anchoring means, and the like.

XI. The Treatment of Fractures of the Proximal Humerus

The first step in treating a fracture of the proximal humerus according to the subject invention is the reduction of the fracture. Preferably, the fracture will be anatomically reduced such that restoration of the normal length, alignment and articular surface congruancy of the fractured proximal humerus is restored. Fracture reduction techniques suitable for use in the subject invention are well known in the art, see Rockwood & Greens's Fractures in Adults (1991) supra (the disclosure of which is herein incorporated by reference) and include both closed and open reduction techniques. Depending on the nature of the fracture, as well as the manner in which it is reduced, fracture reduction may result in the formation of a void or open space in the cancellous bone of the fracture region, where such a void is the result of compression of the cancellous bone during fracture without decompression of such bone upon fracture reduction.

The next step in the subject methods is the preparation of a cancellous bone fracture void. Cancellous bone fracture void preparation comprises at least producing a fracture void in the cancellous bone of the proximal humerus in the region of the fracture, where the void will usually traverse (i.e. span, bridge, cross-over) the fracture line so as to be produced in portions of the cancellous bone on both sides of the fracture line.

In those instances where the reduction of the fracture results in a bone void, the cancellous bone fracture void is prepared by at least expanding the volume of the void which is already present as a result of the fracture reduction. By at least expanding the already present void is meant that the void volume is increased by at least about 300%, usually by at least about 500% and more usually by at least about 1000% from its initial volume following fracture reduction, where the fracture void may be expanded all the way out to the cortices of the proximal humerus, proximally, radially and distally. The void volume may be expanded using any convenient means capable of compressing the cancellous bone in the void. For example, one could employ a rongeur awl, and the like.

Preparation of the cancellous bone fracture void also comprises those embodiments of the subject invention where the cancellous bone is removed and/or compressed in the region of the proximal humerus in a manner sufficient to produce a cancellous bone void which has a fracture stabilizing shape, where the term fracture stabilizing refers to a shape that serves to provide internal stabilization to the fracture and includes cementing, filling the void and the like, where shapes approximating the inner surface of the cortical bone of the proximal humerus in the region of the fracture are preferred.

During preparation of the cancellous void volume, the void may be cleared of any tissue, fluid or other material one or more times during the preparation, as needed, using any convenient means, such as suction, Frazier tip, forceps and the like, where such clearing may further comprise the introduction of a biologically compatible solution which assists in the clearing, such as a saline solution, water, Ringer's solution and the like, where the solution may be cooled in order to reduce the temperature of the void. When cooled solutions are employed, the temperature of such solutions will typically range from about 5 to 37° C., usually from about 5 to 20° C. and more usually from about 15 to 20° C.

Following preparation of the cancellous bone void fracture volume, a structural material as described above, e.g. a flowable calcium phosphate cement capable of setting in vivo into a solid apatite product such as carbonated apatite, is introduced into the prepared cancellous bone fracture void. The structural material may be introduced using any convenient delivery means. The particular delivery means employed will necessarily depend on the nature of the structural material to be introduced into the prepared void. Since the structural material will typically have a flowable paste like consistency, usually a syringe, cannula or other such delivery means will be employed. For use with the preferred flowable calcium phosphate cements, typically the delivery means that is employed will be a needle having a gauge of sufficient size to allow passage of the flowable material. Usually a needle having a gauge ranging from about 8 to 16, usually from about 9 to 16 and more usually from about 12 to 16 will be employed as the delivery means.

The amount of structural material that is introduced into the prepared void will be sufficient to substantially fill the entire void volume, where by substantially fill is meant that the amount introduced will be sufficient to fill at least about 95%, usually at least about 98% and more usually at least about 99% of the void volume and infiltration to adjacent cancellous bone.

Following introduction of the structural material into the prepared void, the structural material will then be allowed to set into a solid product that substantially fills the void volume, where the term substantially fills means the same as defined above. For the preferred calcium phosphate cement of the subject invention, the material will be allowed to set for a period of time of at least about 10 minutes.

Depending on the nature of the structural material, the treatment of the fracture may further comprise immobilization of the proximal humerus at least in the region of fracture for a time sufficient for the structural material to fully harden or cure into a solid product. Any convenient means of immobilization may be employed and will usually comprise the use of a fixation means, where such means include use of casts, where the casts may be fabricated from a variety of different materials, including plaster, polymeric materials, moldable metals and the like, where the preparation and use of casts is well known to those of skill in the art. The subject invention may be used in combination with other fixation means, such as fixation devices, where such devices may be external fixation devices, such as percutaneous fixation devices, e.g. K wires, pins and the like, or internal fixations devices, e.g. bone screws and plates. When used in combination with fixation devices, the fixation devices will preferably not be inserted into or through the structural material, particularly through such materials whose final set properties, such as strength, integrity and the like, might be compromised from removal of the fixation device, e.g. calcium phosphate cements. One fixation means of particular interest for use in combination with the subject methods is what is referred to by those of skill in the art as an Evans staple. When fixation means are employed, they may be employed prior to or after introduction of the structural material into the prepared void, where the particular sequence of introduction employed will necessarily depend on the specific fracture to be treated, the specific fixation means to be used and the particular structural material to be employed.

The subject methods find use in the treatment of fractures of the proximal humerus in a variety of hosts, particularly in mammalian hosts, where such fractures will generally be displaced and may be two-part, three-part and four-part fractures, where two-part fractures are particularly indicated for treatment, with two-part fractures of the surgical neck being more particularly indicated.

XII. Additional Applications

Additional applications in which the flowable cement material prepared by the subject invention may be employed include: vertebral fusions; acetabular fractures; pelvic fractures; total joint arthroplasty, both primary and revision and the like.

As mentioned above, the cement prepared by the subject invention also finds use in dental and craniomaxillofacial applications. Such applications include: the treatment of periodontal osseous defects; the filling of tooth root sockets; the filling and sealing of the root canal system; the fixation of dental implants; in periodontal reconstruction; and in craniomaxillofacial and skull base surgery.

In the treatment of periodontal osseous defects, the flowable cement material is used to fill alveolar bone deficits, reduce periodontal pocket depth and stabilize the tooth, facilitating natural restoration of the periodontum by supporting gingival tissue. Initially, at the time of implantation, it provides structure and a scaffold for new bone formation and in time is replaced by host bone.

As mentioned above, the cement can also be used to fill tooth root sockets following tooth extraction, either at the time of initial extraction to prevent potential abscess or "dry socket" syndrome, or as a secondary procedure in the treatment of such socket related morbidity.

Endodontic use of the flowable cement material includes filling and sealing of the root canal system following removal and cleaning of the root system to induce apical closure and prevent leakage. Because the cement hardens in a fluid environment it can be advantageous over conventional materials used in such applications, such as the gutta-percha, particularly in areas of limited access and in areas that are difficult to maintain in a dry field.

The flowable cement material can be used to enhance immediate fixation of dental implants in mandibular or maxillary bone. The cement is used in such applications by filling any voids at the bone implant interface due to surgical inaccuracies. Routinely dental implants are a two step procedure, the first step being implantation of the osseous implant followed by a number of months prior to seating of the tooth. Improvement in implant fixation with the subject cement material may permit a one stage procedure eliminating the need for a edentulous period which is conventionally required for osseous integration on the implant.

The subject cements can be used in periodontal reconstruction to preserve the alveolar ridge and prevent ridge collapse following tooth extraction or augment the edentulous alveolar ridge following extraction or prior to dental implantation. In such applications, the cement can be injected into resulting osseous defects at the time of tooth extraction or onto prepared bone beds as onlay augmentations to reduce the number of surgeries and achieve the desired ridge architecture.

In craniomaxillofacial and skull base surgery, the subject cements can be used to fill and offer structurally integrity to craniomaxillofacial osseous defects caused by osteotomy, fracture, surgically induced burr holes, congenital deformity and/or neoplastic disease. Other uses of the subject cements in CMF and skull base surgical applications includes augmentation of conventional ORIF hardware fixation, sinus obliteration, and sealing of cerebrospinal fluid (CSF) leaks.

Other dental applications in which the subject cements may find use include those described in U.S. Pat. Nos. 5,695,339; 5,622,552; 5,462,356; 5,427,613; 5,415,547; 5,382,284; 5,367,002; 5,346,717; 5,338,773; 5,336,700; 5,213,615; 5,154,613; 5,104,321; 5,009,593; 4,386,912; and 4,280,842, the disclosures of which are herein incorporated by reference.

It is evident from the above results and discussion that an improved system for storing, preparing and delivering a calcium phosphate cement structural material to a physiological site of interest is provided. The subject system provides for long term storage of the two component cement is a sterile and convenient format. Furthermore, because the components of cement are combined in an enclosed sterile environment of the storage means, the cement may be prepared with the mixing device in a non-sterile field and then transferred conveniently to the sterile field of operation with the convenient and easy to use delivery device.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. A mixing device for mixing a two component cement present in a storage means comprising: (a) a first compartment comprising said liquid component; (b) a second compartment having rounded corners and comprising said dry component; (c) a first frangible barrier separating said first and second compartments; (d) a third elongate compartment capable of receiving a product produced upon combination of said dry and liquid components; and (e) a second frangible barrier separating said second and third compartments; said device comprising:

a positioning means for holding said storage means in position;

a means for moving said liquid component from said first compartment to said second compartment through said frangible seal;

a means for thoroughly combining said liquid component with said dry component in said second compartment to produce a flowable product substantially free of uncombined dry and liquid components; and a means for moving said flowable product from said second compartment to said third compartment through said second frangible seal.

2. The device according to claim 1, wherein said device further comprises an actuation means.

3. The device according to claim 1, wherein said means for moving said liquid component into said second compartment comprises a planar surface.

4. The device according to claim 1, wherein said means for mixing said dry and liquid components is capable of introducing shear force to the contents of said second compartment.

5. The device according to claim 1, wherein said means for mixing said dry and liquid components comprises at least two grooved rollers.

6. The device according to claim 5, wherein said device further comprises a means for randomizing the movement of said at least two grooved rollers.

7. The device according to claim 1, wherein said means for moving said flowable product from said second to said third compartments comprises a squeegee.

8. The device according to claim 1, wherein said positioning means comprises a substantially planar surface with a depressed region at one end capable of holding at least a portion of said third elongate compartment.

9. A mixing device for mixing a two component cement present in a storage means according to claim 6, said device comprising:

a positioning means for holding said storage means in position;

a means for moving said liquid component from said first compartment to said second compartment through said frangible seal;

a means for thoroughly combining said liquid component with said dry component in said second compartment to produce a flowable product;

a means for moving said flowable product from said second compartment to said third compartment through said second frangible seal; and an actuation means.

10. The device according to claim 9, wherein said means for moving said liquid component into said second compartment comprises a planar surface.

11. The device according to claim 9, wherein said means for mixing said dry and liquid components is capable of introducing shear force to the contents of said second compartment.

12. The device according to claim 11, wherein said means for mixing said dry and liquid components comprises at least two grooved rollers.

13. The device according to claim 12, wherein said device further comprises a means for randomizing the movement of said at least two grooved rollers.

14. The device according to claim 9, wherein said means for moving said flowable product from said second to said third compartments comprises a squeegee.

15. The device according to claim 9, wherein said means for holding said storage means in position comprises a substantially planar surface with a depressed region at one end capable of holding at least a portion of said third compartment.

16. The device according to claim 9, wherein said actuation means is electronic.

17. The device according to claim 9, wherein said actuation means is pneumatic.

18. The device according to claim 9, wherein said device further comprises a power source.

19. The device according to claim 18, wherein said power source is a battery.

* * * * *